(12) United States Patent
Rhodes et al.

(10) Patent No.: US 10,064,909 B2
(45) Date of Patent: *Sep. 4, 2018

(54) COMPOSITIONS AND METHODS FOR CHRONIC USE OF A WEIGHT-GAINING COMPOUND

(71) Applicant: Aratana Therapeutics, Inc., Leawood, KS (US)

(72) Inventors: Linda Rhodes, Kansas City, KS (US); Marie-Paul Lachaud, Paris (FR); Bill Zollers, Kansas City, KS (US); Ernst Heinen, Kansas City, KS (US)

(73) Assignee: ARATANA THERAPEUTICS, INC, Leawood, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/601,240

(22) Filed: May 22, 2017

(65) Prior Publication Data
US 2017/0281712 A1    Oct. 5, 2017

Related U.S. Application Data

(63) Continuation of application No. 15/007,525, filed on Jan. 27, 2016, now Pat. No. 9,700,591.

(60) Provisional application No. 62/108,902, filed on Jan. 28, 2015.

(51) Int. Cl.
| | |
|---|---|
| *A61K 38/05* | (2006.01) |
| *G01N 33/74* | (2006.01) |
| *A23K 50/40* | (2016.01) |
| *A23K 20/111* | (2016.01) |
| *A23K 20/132* | (2016.01) |
| *A23K 20/137* | (2016.01) |
| *A23K 50/20* | (2016.01) |
| *A23K 50/10* | (2016.01) |
| *A23K 50/30* | (2016.01) |
| *A23K 20/184* | (2016.01) |

(52) U.S. Cl.
CPC ............ *A61K 38/05* (2013.01); *A23K 20/111* (2016.05); *A23K 20/132* (2016.05); *A23K 20/137* (2016.05); *A23K 20/184* (2016.05); *A23K 50/10* (2016.05); *A23K 50/20* (2016.05); *A23K 50/30* (2016.05); *A23K 50/40* (2016.05); *G01N 33/74* (2013.01); *G01N 33/743* (2013.01); *G01N 2333/61* (2013.01); *G01N 2333/65* (2013.01); *G01N 2800/52* (2013.01)

(58) Field of Classification Search
None
See application file for complete search history.

(56) References Cited

U.S. PATENT DOCUMENTS

| | | |
|---|---|---|
| 2002/0086865 A1 | 7/2002 | Friedman et al. |
| 2008/0300194 A1 | 12/2008 | Mann et al. |
| 2009/0170757 A1 | 7/2009 | Fraser et al. |
| 2009/0221689 A1 | 9/2009 | Marsault et al. |
| 2010/0249228 A1 | 9/2010 | Dalton et al. |
| 2012/0095057 A1 | 4/2012 | Nishida et al. |
| 2012/0202759 A1 | 8/2012 | Pan |
| 2012/0322821 A1 | 12/2012 | Shimada et al. |

FOREIGN PATENT DOCUMENTS

| | | |
|---|---|---|
| CA | A1-2095786 | 11/1993 |
| RU | A-2007129408 | 2/2009 |
| RU | A-2009115711 | 11/2010 |
| RU | C2-2459831 | 11/2010 |
| RU | A-2010111849 | 10/2011 |
| WO | WO2008/039415 | 4/2008 |
| WO | WO2009/030755 | 3/2009 |
| WO | WO2014/052780 | 4/2014 |

OTHER PUBLICATIONS

Carpino et al., Pyrazolinone-piperidine Dipeptide Growth Hormone Secretagogoues (GHSs): Discovery of Capromorelin, Bioorganic & Medicinal Chemistry, 2003, vol. 11, pp. 581-590.
Chinese Office Action related to Application No. 201380061931.6, dated Jan. 3, 2017, 18 pages.
Communication pursuant to Rule 164 (1) EPC, EP Appl. No. 1341455.2, dated Jun. 23, 2016, 7 pages.
Heidi et al., "Effects of an Oral Growth Hormone Secretagogue in Older Adults," Journal of Clinical Endocrinology and Metabolism, 2009, pp. 1198-1206, vol. 94, No. 4.
Hersch et al., "Growth hormone (GH) releasing hormone and GH secretagogues in normal aging: Fountain of Youth or Pool of Tantalus," Clinical Interventions in Aging, 2008, vol. 3, No. 1, pp. 121-129.
International Search Report and Written Opinion related to PCT/US2013062227, dated Sep. 27, 2013, 19 pages.
Martinez et al., "Applying the biopharmaceutics classification system to veterinary pharmaceutical products Part II. Physiological considerations," Advanced Drug Delivery Reviews, 2002, vol. 54, pp. 825-850.
Notice of Allowance and Fee(s) Due, related to U.S. Appl. No. 15/007,525, dated Apr. 19, 2017, 15 pages.
Office Action related to U.S. Appl. No. 15/007,525, dated Dec. 13, 2016, 15 pages.
Pan et al., "Preclinical Pharmacology of CP-424,391, an Orally Active Pyrazolinone-Piperidine Growth Hormone Secretagogue,", 2001, Endocrine, vol. 14, No. 1, pp. 121-132.
Patent Examination Report No. 1, related to AU Appl. No. 2013323349, dated Mar. 22, 2016, 7 pages.
Quiroga, "Anti-Aging Medicine as it Relates to Dermatology," Cosmetic Dermatology, 2005, Chapter 1, 177 pages.
Response to Non-Final Office Action, related to U.S. Appl. No. 15/007,525, dated Mar. 24, 2017, 19 pages.

(Continued)

*Primary Examiner* — Jeanette M Lieb
(74) *Attorney, Agent, or Firm* — Polsinelli PC

(57) ABSTRACT

Provided herein is a method of binding growth hormone secretagogue receptors in one or more companion animals or livestock to stimulate hunger independent of release of growth hormone. The method can provide administering a therapeutically effective amount of a capromorelin-containing composition to a companion animal or livestock in need thereof for a period of at least 30 days. Optionally, one or more flavoring agents or flavor-masking agents can be added to the capromorelin-containing composition to enhance or mask the flavoring of the composition for the companion animal or livestock.

18 Claims, 14 Drawing Sheets

(56) References Cited

OTHER PUBLICATIONS

Riviere et al., "Veterinary Pharmacology and Therapeutics", Ninth Edition Chapter 3, Pharmacokinetics, 2009, pp. 47-73.
Russian Office Action related to Application No. 2015114996/13(023450), dated Feb. 17, 2017, 42 pages.
SciFinder; CAS Registry No. 193273-66-4; accessed Mar. 7, 2016.
Sharma et al., "To scale or not to scale: the principles of dose extrapolation," British Journal of Pharmacology, 2009, vol. 157, pp. 907-921.
West et al., "Lysergic Acid Diethylamide: Its Effects on a Male Asiatic Elephant," Science, 1962, vol. 138, pp. 1100-1103.
White, et al., "Effects of an Oral Growth Hormone Secretagogoue in Older Adults," J Clin Endocrinol Metab., 2009, vol. 94 pp. 1198-1206.

*  AT-002 had significantly different GH levels at 0h vs 8h (p<0.05).
^  Change from 0h to 8h was significantly different between AT-002 vs Placebo (p<0.05).

Treatment by study day interaction was statistically significant (p<0.05).
* AT-002 had significantly different IGF-1 levels at 0h vs 8h (p<0.05).

COMPOSITIONS AND METHODS FOR CHRONIC USE OF A WEIGHT-GAINING COMPOUND

CROSS-REFERENCE

This application claims the benefit under 35 U.S.C. § 119(e) of U.S. Provisional Application Ser. No. 62/108,902, filed Jan. 28, 2015, and entitled "Compositions and Methods for Chronic Use of a Weight-gaining Compound," and is a continuation of U.S. Ser. No. 15/007,525, filed Jan. 27, 2016, and entitled "Compositions and Methods for Chronic Use of a Weight-gaining Compound," the disclosures of which are incorporated by reference in their entireties.

TECHNICAL FIELD

The present disclosure relates to a weight-gaining compound and methods for chronic use thereof to control weight in animals. In particular, the current disclosure is directed to a novel use of an weight-gaining compound to potentially induce increased food intake, lean muscle growth, and increased weight gain in animals suffering from chronic inappetance or other chronic maladies or disorders that induce weight loss, frailty, and/or wasting for periods of eight days or greater.

BACKGROUND

Like humans, companion animals and livestock can suffer from chronic inappetance and other disorders that can result in loss of lean muscle, an inability to participate in physical activity, weight loss, and other undesirable outcomes for the companion animal and the owner. For instance, companion animals and/or livestock undergoing chemotherapy or afflicted with cancer, heart disease, or chronic kidney disease can suffer from chronic inappetance, weight loss, general frailty, and/or cachexia. Moreover, the conditions or afflictions inducing the chronic inappetance, weight loss, general frailty, and/or cachexia can be at least partially exacerbated by the fact that the diets of these animals consist of fewer calories, vitamins, minerals, protein, and other necessary nutritional components, due to the decrease in food intake. As a result, these animals can exhibit a decrease in lean muscle, general weakness including a weakened immune system, possibly making the animals susceptible to infections.

Furthermore, although a general increase in food consumption could be helpful to animals, it is important that these animals do not experience a significant increase in deposition of adipose tissue. Accordingly, it would be desirable to have a composition and a method of using the composition to control weight loss while not inducing a significant increase in adipose tissue. To date, there are no approved veterinary active pharmaceutical ingredients for the treatment of chronic inappetance, unwanted weight loss, general frailty, wasting, and other related afflictions, complications, and maladies. As such, it is desired to have a compound or treatment for use in controlling weight in animals, including companion animals and livestock.

SUMMARY

The present disclosure relates to compositions and methods of chronic use of a weight-gaining compound. For example, the weight-gaining compound can comprise a ghrelin agonist, such as a capromorelin-containing composition and can be administered to one or more companion animals (e.g., dogs, cats, or horses) or livestock in a therapeutically effective amount for a period of at least 8 days to treat weight loss. The inventors have surprisingly discovered that mean percent bodyweight changes that were statistically significantly increased when compared to placebo after period of capromorelin administration for at least 8 days, such as at least 15 days, or at least 21 days. In short, administrating the capromorelin-containing formulation for at least 8 days results in unexpected, surprising, and statistically significant increase in weight gain compared to the same administration for only 7 days or less, and a consistent baseline of clinically relevant markers of drug activity after 4 days of treatment, including IGF-1.

The capromorelin-containing composition can be administered to a companion animal or livestock in need thereof through a variety of different pathways, including an oral cavity or intravenously, and can be administered at least once or twice per day during the treatment regimen.

As disclosed herein, the capromorelin-containing composition can include a dose of between about 0.5 milligrams and 60 milligrams of capromorelin per kilogram of bodyweight of the animal per day. The compound can be a pill or a liquid and can be flavored to cover up any unpleasant or bitter taste. Moreover, the capromorelin-containing composition can be administered to the companion animals or livestock in conjunction with a chemotherapeutic regimen to treat cancer, to at least partially prevent, inhibit, control, and/or alleviate weight loss associated with the chemotherapy.

Specifically, the present disclosure provides a method of increasing lean muscle mass, increasing weight gain, and alleviating weight loss in a non-human animal by orally administering a therapeutically effective dose of a capromorelin composition for a period of at least 8 days, which may further include one or more flavoring agents or flavor-masking agents. The therapeutically effective dose of the capromorelin composition can induce the non-human animal or livestock in need thereof to consume greater amounts of food relative to those "patients" not receiving the capromorelin composition. The capromorelin composition can include a dose of between about 0.5 milligrams and 60 milligrams of capromorelin per kilogram of bodyweight of the non-human animal per day. Moreover, the capromorelin composition can be administered to the non-human animal in conjunction with a chemotherapeutic regimen to treat cancer to at least partially prevent, inhibit, control, and/or alleviate weight loss associated with the chemotherapy.

Also provided herein is a method of treating a non-human animal with weight loss. The method can include determining that a non-human animal is experiencing weight loss and administering at least one daily dose of a capromorelin-containing composition to the non-human animal for a period of at least 8 days. The method can further provide obtaining a marker of drug effect (e.g., food consumption, bodyweight, lean muscle mass, etc.) or a sample from the non-human animal and measuring an amount of at least one marker of drug effect (e.g., levels of insulin-like growth factor, growth hormone, cortisol, etc.) in the sample. For example, the dose of the capromorelin-containing composition can be increased to correspondingly increase the amount insulin-like growth factor-1 in the sample. The dose of the capromorelin-containing composition can be decreased to correspondingly decrease the amount of cortisol in the sample. Moreover, the sample can comprise a blood, plasma, or serum sample from the non-human animal.

The present disclosure also provides another method of treating weight loss in a companion animal or livestock. The method can include determining that a companion animal or livestock is experiencing weight loss and administering at least one daily dose of a capromorelin-containing composition to the animal using a syringe for a period of at least 8 days. The method can further include assessing one or more markers of the animal that are associated with weight loss and adjusting the dose of the capromorelin-containing composition in light of the assessment of the one or more markers. The pharmaceutical composition can be administered to the companion animal at least once or twice per day. The composition can include a dose of between about 0.5 milligrams to about 60 milligrams of capromorelin per kilogram of bodyweight of the companion animal per day. Furthermore, the one or more markers can include bodyweight of the companion animal or food intake of the companion animal. Moreover, the composition can be administered to the companion animal or livestock through at least one of the following routes of administration: oral, intravenous, intramuscular, subcutaneous, or intraperitoneal.

In another aspect, the present disclosure also provides a method of treating weight loss in a companion animal or livestock. The method comprises administering a therapeutically effective amount of a capromorelin-containing composition to a companion animal or livestock in need thereof at least once per day for a period of at least 30 days, such as at least 90 days. The capromorelin-containing composition comprises a dose of from about 0.5 milligrams to about 7.5 milligrams of capromorelin per kilogram of bodyweight of the companion animal or livestock per day. The companion animal or livestock is chosen from dog, cat, or horse.

In yet another aspect, the present disclosure provides a method of increasing lean muscle mass, alleviating weight loss, and increasing weight gain in a non-human animal. The method comprises orally administering a therapeutically effective dose of a capromorelin composition to a non-human animal in need thereof at least once per day for a period of at least 30 days, such as at least 90 days. The capromorelin composition comprises one or more flavoring agents or masking agents comprising at least one agent selected from the group consisting of thaumatin, sucralose, neotame, sodium saccharain, neohesperidin dihydrochalcone, rebaudioside A, steviol glycoside, licorice, glycyrrhizic acid, monoammonium glycyrrhizinate, sucrose, glucose, fructose, maltodextrin, sorbitol, maltitol, isomalt, glycerol, and a vanilla-comprising composition. The capromorelin composition comprises a dose of between about 0.5 milligrams and about 7.5 milligrams of capromorelin per kilogram of bodyweight of the non-human animal per day. The therapeutically effective dose of the capromorelin composition causes the animal to consume a greater amount of food; and wherein the non-human animal is chosen from dog, cat, horse, or livestock.

In other aspects, the present disclosure provides a method of treating weight loss in a non-human animal comprising the steps of: determining that a non-human animal is experiencing weight loss; administering at least one dose of a capromorelin-containing composition to the non-human animal at least once per day for a period of at least 30 days, such as at least 90 days; obtaining a sample comprising a blood, plasma or serum sample from the non-human animal; measuring an amount of at least one marker of drug effect in the sample, the marker comprising at least one of insulin-like growth factor-1, cortisol, growth hormone and/or capromorelin; and adjusting the dose of the capromorelin-containing composition in light of the amount of the marker in the sample. The dose of the capromorelin-containing composition comprises a dose of between about 0.5 milligrams and about 7.5 milligrams of capromorelin per kilogram of bodyweight of the non-human animal per day.

In still other aspects, the present disclosure provides a method of treating weight loss in at least one of a companion animal and livestock comprising the steps of: determining that a companion animal or livestock is experiencing weight loss; administering at least one daily dose of a capromorelin-containing composition to the companion animal or livestock at least once per day for a period of at least 30 days, such as at least 90 days; assessing one or more markers of the companion animal or livestock that are associated with weight loss, the markers comprising change in weight of the companion animal or livestock, change in food intake of the companion animal or livestock, and change in lean muscle mass; and adjusting the dose of the capromorelin-containing composition in light of the assessment of the one or more markers.

In yet other aspects, the present disclosure provides a method of treating weight loss in a companion animal or livestock comprising: orally administering a pharmaceutical composition comprising capromorelin at least once per day to a companion animal or livestock in need thereof at least once per day for a period of at least 30 days, such as at least 90 days; and determining effectiveness of the pharmaceutical composition by observing one or more markers of the companion animal or livestock, the markers comprising at least one of bodyweight of the companion animal and food intake of the companion animal or livestock. The pharmaceutical composition comprises a dose of between about 0.5 milligrams and 7.5 milligrams of capromorelin per kilogram of bodyweight of the companion animal or livestock per day.

In still other aspects, the present disclosure provides a method of treating weight loss in a non-human animal comprising: providing a vessel comprising a pharmaceutical composition that includes capromorelin; withdrawing about one dose of the pharmaceutical composition from the vessel; and administering the pharmaceutical composition using the syringe to a non-human animal in need thereof at least once per day for a period of at least 30 days, such as at least 90 days.

Further, the present disclosure provides a method of the management of weight loss in cats with chronic kidney disease. The method comprises administering a therapeutically effective amount of a capromorelin-containing composition to a cat diagnosed chronic kidney disease and in need thereof at least once per day for a period of at least 30 days. The capromorelin-containing composition comprise from about 0.5 milligrams to about 7.5 milligrams of capromorelin per kilogram of bodyweight of the cat per day.

The present disclosure also provides a method of treating cachexia, such as cardiac cachexia, in non-human animals, such as companion animals and livestock. The method comprises administering a therapeutically effective amount of a capromorelin-containing composition to a non-human animal diagnosed cachexia (such as cardiac cachexia) and in need thereof at least once per day for a period of at least 30 days. The capromorelin-containing composition comprise from about 0.5 milligrams to about 7.5 milligrams of capromorelin per kilogram of bodyweight of the cat per day.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

BRIEF DESCRIPTION OF THE DRAWINGS

In addition to the exemplary aspects and embodiments described above, further aspects and embodiments will become apparent by reference to the drawings and by study of the following descriptions.

DETAILED DESCRIPTION

Figure 1:
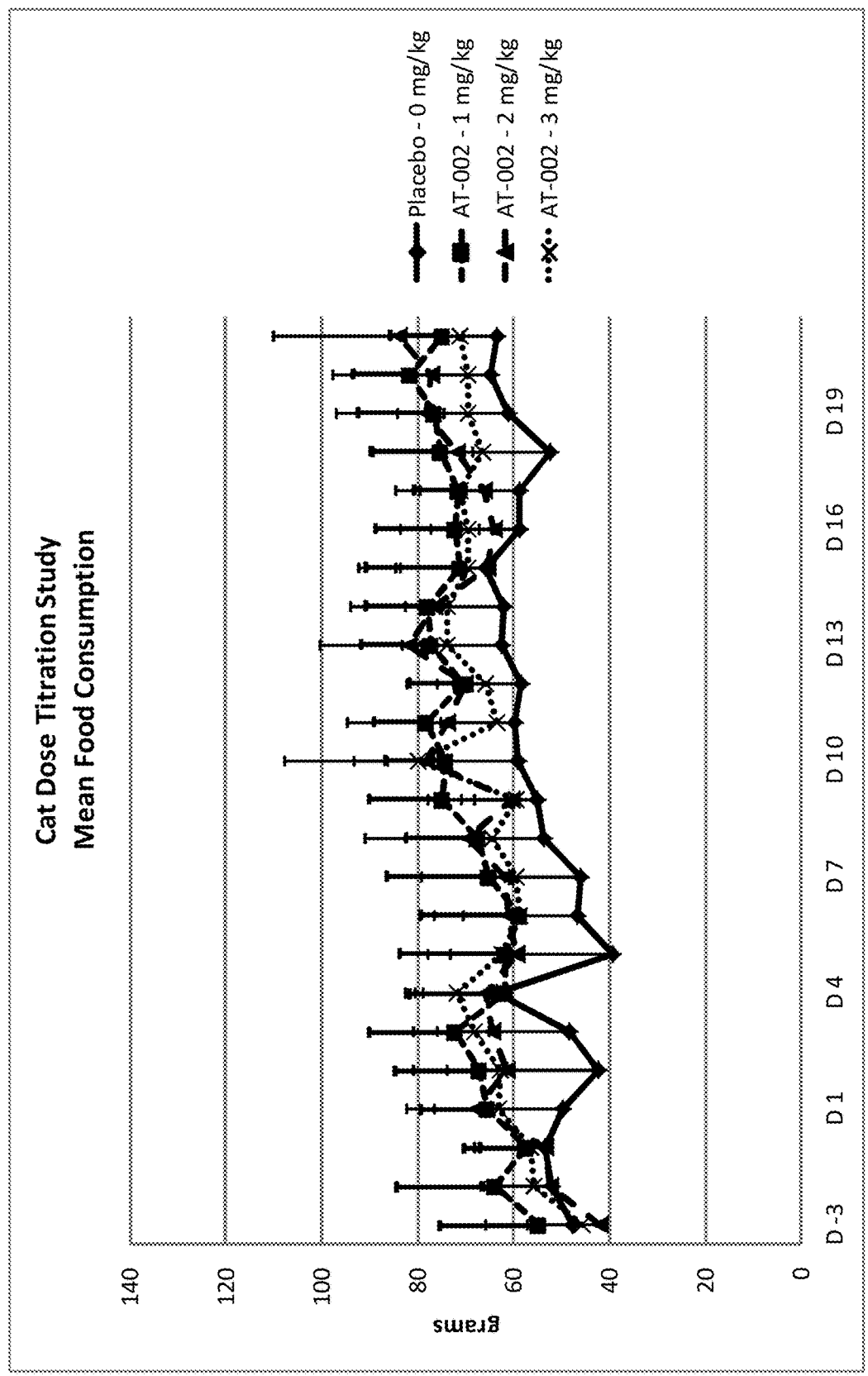
FIG. 1 depicts mean food consumption in grams over time for the cat dose titration study, as described in Example 2. The mean food consumption is compared for placebo and capromorelin (AT-002) doses at 1 mg/kg, 2 mg/kg, and 3 mg/kg.

The methods and compositions provided herein can be used for treatment, prevention, alleviation, and/or control of weight loss in animals, including companion animals, livestock, a variety of mammals, and avian species. As such, upon administration to these animals, the compositions can induce the production of one or more molecules that can cause the companion animal to experience a hunger sensation, especially for periods of treatment of at least 8 days. Moreover, without wishing to be bound by theory, administration of the compositions to the animals can also induce one or more molecules that increase lean muscle mass so that the food consumed as a result of the increased hunger sensation can be used in building lean muscle in lieu of adipose deposition.

The compositions can comprise a ghrelin agonist, such as capromorelin, and may include at least one flavoring agent or a flavor-masking agent. In addition, the present disclosure is based on, at least in part, the finding that treatment of companion animals and livestock afflicted with weight loss that receives one or more doses of composition for at least 8 days exhibit statistically significant increased bodyweights, increased food consumption, and increased serum levels of one or more relevant proteins and/or other molecules, such as, but not limited to, insulin-like growth factor-1 (herein "IGF-1"), growth hormone (herein "GH"), and/or cortisol. Specifically, administrating the capromorelin-containing formulation for at least 8 days results in unexpected, surprising, and statistically significant increase in weight gain compared to the same administration for only 7 days or less, and a consistent baseline of clinically relevant markers after 4 days, including serum IGF-1.

The compositions for the management of chronic weight loss or increased weight gain can include capromorelin, which includes racemates, polymorphs, solvates, enantiomers, salts, and any other suitable pharmaceutically acceptable derivative of capromorelin. Capromorelin is also known as N-[(2R)-1-[(3aR)-2-methyl-3-oxo-3a-(phenylmethyl)-6,7-dihydro-4H-pyrazolo[4,3-c]pyridin-5-yl]-1-oxo-3-(phenylmethoxy)propan-2-yl]-2-amino-2-methylpropanamide L-tartrate. In addition, capromorelin has the following chemical structure:

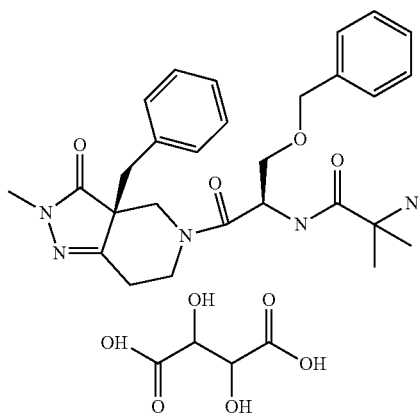

In some companion animals and livestock, ghrelin is a hormone produced predominantly in the glandular stomach and other portions of the alimentary canal and is the endogenous ligand of the ghrelin receptor, which is also known as the growth hormone secretagogue receptor (GHS-R). Not wishing to be bound by theory, GHS-Rs can be expressed in multiple tissues, including neurological tissues, such as, but not limited to the pituitary gland and the hypothalamus. Ghrelin exhibits a relatively short half-life (e.g., approximately ten minutes) in the blood of animals, including companion animals and livestock, and begins accumulating in the blood shortly after completion of a meal. Accordingly, the longer period of time since the last meal of the animal, the greater the concentration of ghrelin in the blood. Moreover, once sufficient amounts of ghrelin bind the GHS-Rs in the hypothalamus, the animals begin feeling hunger, which stimulates food intake.

In addition to binding GHS-Rs in the hypothalamus, circulating ghrelin can also bind GHS-Rs in the pituitary gland to stimulate the release of GH. Furthermore, and not wishing to be bound by theory, in addition to the release of GH originating from ghrelin binding the GHS-Rs in the pituitary gland, animals naturally secrete GH in a circadian rhythm. Although this natural release is present throughout the life of the animal, the magnitude of the release of pulses of GH diminishes over the course of the life of the animal. The released GH can circulate through the companion animal, which can induce the production and secretion of IGF-1 into circulation. The increase in circulating IGF-1 levels can induce lean muscle growth, which can be correlated with increased strength, stamina, and well-being.

Moreover, in addition to inducing GH production, ghrelin can also induce production of cortisol, which has been shown to increase the likelihood of fat deposition in adipose tissue.

When administered to an animal, such as a companion animal or livestock, capromorelin can function as a GHS-R agonist to control chronic inappetance, weight loss, anorexia, and/or cachexia. In particular, capromorelin can be used to treat cachexia, such as cardiac cachexia. Specifically, the administration of capromorelin can induce appetite stimulation and secretion of GH, especially when administered for at least 8 days. Unlike endogenous ghrelin, capromorelin typically exhibits a longer half-life in circulation and unlike exogenous ghrelin, capromorelin is biologically active when orally administered.

Capromorelin compositions can be orally administered to the animals and cause the biological effects of stimulating appetite, food intake, GH release, etc. As discussed in greater detail below, capromorelin compositions can also be administered via other routes (e.g., intravenous, intraperitoneal, intramuscular, intrathecal, subcutaneous, and any other suitable route of administration).

Moreover in addition to or in lieu of capromorelin, at least some of the pharmaceutical compositions can also include other ghrelin-like compounds (e.g., agonists of GHS-R) to treat and/or at least partially alleviate chronic weight loss. For example, at least some of the non-capromorelin ghrelin-like compounds can similarly bind to GHS-Rs to induce a hunger sensation and stimulate food intake in the animals that receive these compounds. These compounds can be any other suitable agonist that binds the GHS-R.

The pharmacologic mechanism of action of capromorelin operates similarly to the mechanism of ghrelin. For example, after administration, capromorelin binds to GHS-R, a G-protein-coupled receptor that can activate protein kinase C and stimulate GH release from the pituitary gland, which can result in the elevation of circulating GH. Without wishing to be bound by theory, GH can then cause the release of IGF-1, which may induce negative feedback to the pituitary gland, thereby reducing or inhibiting GH release. As previously mentioned, IGF-1 also acts to increase lean body mass. Moreover, the administration of capromorelin can supplement the diminishing natural release of GH over the life of the animal. In addition, the negative feedback arising from the circulating IGF-1 can also reduce levels of circulating cortisol, thereby at least partially reducing the likelihood of increased adipose deposition.

Generally, the period of administration for capromorelin can and will vary. The capromorelin may be provided at a concentration suitable to treat the non-human animal in need thereof for at least 8 days. The capromorelin may be provided at a concentration suitable to treat the non-human animal in need thereof for about 8 days, for about 9 days, for about 10 days, for about 11 days, for about 12 days, for about 13 days, for about 14 days, for about 15 days, for about 16 days, for about 17 days, for about 18 days, for about 19 days, for about 20 days, for about 21 days, for about 22 days, for about 23 days, for about 24 days, for about 25 days, for about 26 days, for about 27 days, for about 28 days, for about 29 days, for about 30 days, for about 31 days, for about 32 days, for about 33 days, for about 34 days, for about 35 days, for about 36 days, for about 37 days, for about 38 days, for about 39 days, for about 40 days, for about 41 days, for about 42 days, for about 43 days, for about 44 days, for about 45 days, for about 60 days, for about 75 days, for about 90 days, for about 120 days, for about 150 days, for about 180 days, for about 210 days, for about 240 days, for about 270 days, for about 300 days, for about 330 days, for about 360 days, or for about 365 days.

The capromorelin may be provided at a concentration suitable to treat the non-human animal in need thereof for about 8 days to about 365 days. The capromorelin may be provided at a concentration suitable to treat the non-human animal in need thereof at least 14 days. The capromorelin may be provided at a concentration suitable to treat the non-human animal in need thereof at least 21 days. The capromorelin may be provided at a concentration suitable to treat the non-human animal in need thereof at least 30 days. The capromorelin may be provided at a concentration suitable to treat the non-human animal in need thereof at least 90 days.

The capromorelin may be provided at a concentration suitable to treat the non-human animal in need thereof less than 365 days. The capromorelin may be provided at a concentration suitable to treat the non-human animal in need thereof less than 90 days. The capromorelin may be provided at a concentration suitable to treat the non-human animal in need thereof less than 30 days. The capromorelin may be provided at a concentration suitable to treat the non-human animal in need thereof less than 21 days.

The capromorelin may be provided at a concentration suitable to treat the non-human animal in need thereof for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

Capromorelin can be included within the weight-gaining composition in one or more concentrations. The capromorelin can be at least partially dissolved in an aqueous solvent (e.g., deionized and/or purified water). For example, the concentration of capromorelin within the weight-gaining composition can be within the range of about 0.01 milligrams of capromorelin per kilogram of animal bodyweight (hereinafter "mg/kg") to about 75 mg/kg. Surprisingly, the administration capromorelin at high doses (e.g. greater than 40 mg/kg) daily for an entire year resulted in favorable toxicology.

For example, the capromorelin concentration can be within the range of about 0.1 mg/kg to about 7.5 mg/kg. The range of capromorelin concentration can be between about 1 mg/kg to about 60 mg/kg. Alternatively, the range of capromorelin concentration can be between about 0.5 mg/kg to about 7.5 mg/kg. The range of capromorelin concentration can be between about 0.75 mg/kg to about 6 mg/kg.

By way of further example, the concentration of capromorelin can be at least one of 0.75 mg/kg, 1.0 mg/kg, 2.0 mg/kg, 3.0 mg/kg, 4.0 mg/kg, 5.0 mg/kg, 6.0 mg/kg, and any concentrations in between. The range of capromorelin concentration can be between about 2 mg/kg to about 6 mg/kg. Alternatively, the range of capromorelin concentration can be between about 3 mg/kg to about 4.5 mg/kg. The capromorelin concentration can be about 2 mg/kg. Also, the capromorelin concentration can be about 3 mg/kg.

The number of daily administrations of the capromorelin-containing composition to an animal in need thereof can and will vary. A therapeutically effective amount of the capromorelin-containing composition is administered to the companion animal or livestock at least once per day. A therapeutically effective amount of the capromorelin-containing composition is administered to the companion animal or livestock at least twice per day. Alternatively, a therapeutically effective amount of the capromorelin-containing composition is administered to the companion animal or livestock at least thrice per day.

Capromorelin can be at least partially dissolved in an aqueous solvent and the pharmaceutical composition can comprise other non-active ingredients, such as preservatives, emulsifying and/or viscosifying agents, sweeteners, flavoring agents, and/or flavor-masking agents.

Moreover, the concentration of capromorelin within the weight-gaining composition can be at least partially dependent upon the route of administration and/or the number of times in a pre-determined time period the composition is administered to companion animals or livestock. For example, one or more formulations of the composition can be designed for injectable administration. As a result, the capromorelin within the composition can be delivered directly to the circulation (e.g., via intravenous administration), thereby circumventing the need for absorption in the alimentary canal. Accordingly, greater amounts of capromorelin can reach the desired targets (e.g., GHS-Rs) relative to oral formulations, leading to a lower necessary concentration of capromorelin in a sterile injectable version.

The weight-gaining composition can be orally administered one or more times per day. For example, the composition can be administered as a solution, a solid, or a preferred viscous liquid formulation. Correspondingly, the greater number of times per day the composition is administered to the companion animals, the lesser the amount of capromorelin is needed to produce desired results.

By way of example only, dosing of the animals can be divided into multiple treatment regimens, depending on severity of the indications of the animal. Animals may receive a 1 mg/kg, 2 mg/kg, 3 mg/kg, 4.5 mg/kg, or 6 mg/kg dosing regimen. The animal may be a cat, and the cat may receive a 2 mg/kg dosing regimen. Specifically, the animal may be a dog, and the dog may receive a 3 mg/kg dosing regimen.

Moreover, some of these dosing regimens may be in the form or solid or liquid formulations. Some animals (e.g., dogs) can receive one or more solid oral formulations, such as weight-gaining composition formulated for administration via capsules, gel caps, gel-like liquids (i.e., viscous liquids), pills, caplets, tablets, or other solid, liquid, or nebulized forms. The capsules or other forms can include different concentrations of capromorelin to enable dosing of animals of a plurality of weights (i.e., because the capromorelin dosing at least partially depends on the weight of the animal).

By way of example only, capsules can be manufactured with a capromorelin concentration of 20 mg per capsule, 35 mg per capsule, and 75 mg per capsule. As a result, different combinations of capsules can be administered to the animals in need of treatment to provide the necessary dose of capromorelin to the animal. By way of example only, an animal weighing approximately 15 kg and placed on a 3 mg/kg treatment regimen would require about 45 mg of capromorelin per dose. Accordingly, the animal can receive two 20 mg capsules to provide a dose of capromorelin that is close to 45 mg (i.e., with between 5 and 10 milligrams of the desired dose based on animal weight or within a dosing band). Other animals of other sizes and placed on other treatment regimens can be similarly treated to provide an efficacious amount of capromorelin.

In addition, the weight-gaining composition can comprise liquid oral formulations that can be used in a manner similar to the above solid oral formulation. For example, the liquid formulations can be prepared to comprise the following concentrations of capromorelin within the liquid formulation: 20 mg/mL, 30 mg/mL, 40 mg/mL, or 60 mg/mL. The liquid formulation may comprise 30 mg/mL capromorelin.

Similar to the solid formulations discussed above, the different concentrations of the liquid formulation can be used to enable dosing of animals of a plurality of weights. As a result, different volumes of the different solutions can be administered to the animals to provide the required dose of capromorelin. By way of example only, an animal weighing approximately 15 kg and placed on a 3 mg/kg treatment regimen would require about 45 mg of capromorelin per dose. Accordingly, the animal can receive about 2.3 mL of the 20 mg/mL solution or 1.1 mL of the 40 mg/mL solution to provide a dose of capromorelin that is close to 45 mg. Similarly, if the same animal was placed on a 4.5 mg/kg treatment regimen, the animal could receive 2.3 mL of the 30 mg/mL solution or 1.1 mL of the 60 mg/mL solution to provide a dose of capromorelin close to 67.5 mg (i.e., the dose a 15 kg animal should receive on this treatment regimen). Other animals of other sizes and placed on other treatment regimens can be similarly treated to provide an efficacious amount of capromorelin.

The weight-gaining composition can be administered using any one of a plurality of routes of administration. The weight-gaining composition can be orally, parenterally, and/or topically administered.

The weight-gaining composition can be orally formulated in a liquid and/or a solid formulation so that the composition can be administered using at least one of a spray, a pill, a tablet, a caplet, or an otherwise liquid administration scheme.

The composition can be for formulated for administration via subcutaneous, intradermal, intravenous, intramuscular, intracranial, intraperitoneal, or intrathecal administration (e.g., via an injection or composition-dispensing pump).

The composition can be formulated for transdermal and/or transmucosal administration (e.g., via a buccal film).

In addition, the weight-gaining composition can be administered intranasally or in the form of one or more suppositories.

The weight-gaining composition can be administered by application to the food eaten by the companion animal or livestock in need thereof.

The weight-gaining composition can be formulated for any other suitable route of administration known in the art.

By way of example only, the composition can be stored in one or more vessels (e.g., a sterile bottle) from which an individual (e.g., a veterinarian and/or a caretaker/owner of the animal) can access the weight-gaining composition. For instance, using a syringe, the individual can withdraw about one dose of the composition (e.g., about five milliliters) from the vessel for administration to the animal.

The individual can secure the animal and place the syringe within the mouth of the animal (e.g., a back corner of the mouth near the back of the tongue). Once prepared, the individual can depress the plunger of the syringe to release the composition into the mouth/oral cavity of the animal so that the animal swallows the composition. As a result of placing the syringe near the rear of the mouth, the animal will nearly involuntarily swallow the composition so that some or all of the composition is received within the alimentary canal of the animal.

Prior to and/or after withdrawing the dose of the weight-gaining composition from the vessel, a needle can be affixed to the syringe and the dose can be administered to the animal through any of the previously mentioned routes of administration.

The weight-inducing composition can comprise a solid-dosage formulation so that the composition can be given in other forms (e.g., pills, caplets, tablets, etc.) with or without food.

The weight-gaining composition can be provided to the individual in a "ready-to-use" formulation. For example, the composition can be provided in the vessel so that the individual is not required to make any further additions to the vessel or treat the composition in any way to prepare the composition for administration to the animal.

The weight-gaining composition can be provided in an emulsified liquid formulation or suspension so that one or more additional compounds, excipients, other materials or preparatory steps may need to be added or carried out to ready the composition for administration to the animal.

The composition can include one or more pharmaceutically acceptable excipients. Some examples of possible excipients include diluents, binders, fillers, buffering agents, pH modifying agents, disintegrants, dispersing agents, stabilizers, preservatives, and/or coloring agents. The amount and types of excipients may be selected according to known principles of pharmaceutical science.

The composition can include one or more flavoring agents and/or flavor-masking agents.

The composition may have an unpleasant or undesirable flavor so that one or more additional compounds may be added to increase palatability.

The weight-gaining composition that may be formulated for oral administration can include one or more of the following flavoring agents and/or flavor-masking agents (e.g., sweetening agents): sucralose; a dispersion of licorice, licorice derivatives, and licorice extract (glycyrrhizic acid/monoammonium glycyrrhizinate); MagnaSweet®; a blend of sodium saccharin and neohesperidin dihydrochalcone (Optisweet™ SD), 97:3 (w/w) mixture of sucrose and maltodextrin (Di-Pac®), thaumatin 7% (sweetener) blended with an inactive maltodextrin (Thaumatin T200X), pure thaumatin (Talin-Pure), stevia extract rebaudioside A (steviol glycosides), neotame, and/or polyols (sugar alcohols), such as sorbitol, maltitol, isomalt, xylitol, and glycerin.

As used herein "MagnaSweet®" refers to a composition consisting essentially of one or more sweeteners selected from the group consisting of glycyrrhizic acid (GA), monoammonium glycyrrhizinate (MAG), rebaudioside A, and glycerin. The MagnaSweet® may consist essentially of glycyrrhizic acid (GA), monoammonium glycyrrhizinate (MAG), rebaudioside A, and glycerin. The MagnaSweet® may consist essentially of glycyrrhizic acid (GA), monoammonium glycyrrhizinate (MAG), and glycerin. The MagnaSweet® may comprise from about 0.5% to about 25% GA/MAG, from about 0% to about 15% rebaudioside A, and from about 75% to about 99.5% glycerin. The MagnaSweet® may comprise from about 1.5% to about 17% GA/MAG, from about 0% to about 7.5% rebaudioside A, and from about 83% to about 91% glycerin. The MagnaSweet® may comprise about 1.5% GA/MAG, about 7.5% rebaudioside A, and about 91% glycerin. The MagnaSweet® may comprise about 9% GA/MAG and about 91% glycerin. The MagnaSweet® may comprise about 17% GA/MAG and about 83% glycerin.

In particular, some sugar-containing sweeteners, such as saccharose-containing materials, sucrose, glucose, fructose, and maltodextrin, may at least partially degrade the capromorelin within the composition. Accordingly, large concentrations of some sugar-containing sweeteners should be avoided.

In addition, the flavoring agents and/or flavor-masking agents can comprise a vanilla-comprising composition, such as, but not limited to ethyl vanillin, vanillin (vanillin-RHD), natural vanilla flavor (vanillin-Merck), nature-identical vanilla flavor (vanilla-TG-old), and suitable solvents (e.g., ethanol and/or water).

The flavoring agents and/or flavor-masking agents can comprise one or more selected from chicken, bacon, beef, pork, liver, fish, honey, caramel, and banana.

The flavoring agents or masking agents can comprise at least one of thaumatin, sucralose, neotame, sodium saccharain, neohesperidin dihydrochalcone, rebaudioside A, steviol glycoside, licorice, glycyrrhizic acid, monoammonium glycyrrhizinate, sucrose, glucose, fructose, maltodextrin, sorbitol, maltitol, isomalt, glycerol, and a vanilla-comprising composition.

The flavoring agents and/or flavor-masking agents can comprise a percent weight per final volume of the weight-gaining composition of between about 50% to about 0.001%, depending on the agent selected.

The flavoring agents and/or flavor-masking agents can comprise a percent weight per final volume of the weight-gaining composition of between about 40% to about 0.01%, depending on the agent selected.

The flavoring agents and/or flavor-masking agents can comprise a percent weight per final volume of the weight-gaining composition of between about 30% to about 0.01%, depending on the agent selected.

The weight-gaining composition can include one or more inactive ingredients that can function to stabilize or buffer the composition, function as an emulsifier or viscosifying agent for at least one or more of the constituents of the composition, function as a vehicle, function as a replacement material for sucrose, function as a solvent, and can function to serve any other desirable role. For example, the weight-gaining composition can include one or more of the following substances: citric acid, sodium citrate, sodium chloride; preservatives, such as methyl 4-hydroxybenzoate salt and propyl 4-hydroxybenzoate salt; neosorb, sorbitol, maltitol, propylene glycol, vegetable glycerin, polyvinylpyrrolidone (Kollidon™ 90F), xanthan gum, Pluriol-E3350®, polyethylene glycol, purified/deionized water, macrogolglycerol hydroxystearate, methylcellulose, and propylene glycol.

The weight-gaining composition can include one or more physiologically acceptable carriers, such as hydrophilic solvents, hydrophobic solvents, for example water for injection (WFI), glycerol, and propylene glycol, buffers, such as citrate, acetate, and phosphate.

The inactive ingredients can comprise a percent weight per final volume of the weight-gaining composition of between about 80% to about 0.001%, depending on the agent selected.

The inactive ingredients can comprise a percent weight per final volume of the weight-gaining composition of between about 40% to about 0.01%, depending on the agent selected.

The inactive ingredients can comprise a percent weight per final volume of the weight-gaining composition of between about 25% to about 0.01%, depending on the agent selected.

The weight-gaining composition can include the following base formulation in a solution.

TABLE 1

Representative ranges for components in the weight-gaining composition.

| Ingredient | % weight per volume |
| --- | --- |
| Capromorelin | 1.0-7.5 |
| Methyl 4-Hydroxybenzoate Salt | 0.045-0.180 |
| Propyl 4-Hydroxybenzoate Salt | 0.005-0.20 |
| Citric Acid (Anhydrous) | 0.7 |
| Sodium Citrate | 0.5 |
| Sodium Chloride | 0.7 |
| Neosorb sorbitol 70% | 30 |
| Maltitol Solution | 25 |
| Vegetable-based Glycerin | 20 |
| Purified Water | q.s. |

Moreover, the following combinations of materials, solutions, compositions, and/or compounds can be added to the base formulation disclosed above to form one or more weight-gaining compositions for administration to treat weight loss, as shown at Tables 2, 3, and 4.

TABLE 2

Formulation Numbers 1-12 of the weight-gaining composition.

| Formulation Number | Concentration of Capromorelin Composition (in mg/mL) | Viscosifying Agent (in % weight per volume) | Sweetener | Flavoring Agent and/or Flavor-Masking Agent |
| --- | --- | --- | --- | --- |
| 1 | 21 | Kollidon 90F (1.5%) | Thaumatin T200X (0.4%); Stevia Rebaudioside A (0.4%); and MagnaSweet ® (0.5%) | Ethyl Vanillin (0.1%) and Ethanol (0.25%) |
| 2 | 21 | Kollidon 90F (1.5%) | Sucralose (0.7%) and MagnaSweet ® (0.5%) | Ethyl Vanillin (0.1%) and Ethanol (0.25%) |
| 3 | 21 | Kollidon 90F (1.5%) | Talin-Pure (0.3%) and MagnaSweet ® (0.5%) | Ethyl Vanillin (0.1%) and Ethanol (0.25%) |
| 4 | 21 | Kollidon 90F (1.5%) | OptisweetSD (0.5%) and MagnaSweet ® (0.5%) | Ethyl Vanillin (0.1%) and Ethanol (0.25%) |

TABLE 2-continued

Formulation Numbers 1-12 of the weight-gaining composition.

| Formulation Number | Concentration of Capromorelin Composition (in mg/mL) | Viscosifying Agent (in % weight per volume) | Sweetener | Flavoring Agent and/or Flavor-Masking Agent |
|---|---|---|---|---|
| 5 | 21 | Xanthan-Gum (0.05%) | Thaumatin T200X (0.4%); Stevia Rebaudioside A (0.4%); and MagnaSweet ® (0.5%) | Vanillin (0.1%) and water |
| 6 | 21 | Pluriol-E3350 ® (7.5%) | Thaumatin T200X (0.4%); Stevia Rebaudioside A (0.4%); and MagnaSweet ® (0.5%) | Ethyl Vanillin (0.13%) and Ethanol (0.3%) |
| 7 | 21 | None | Thaumatin T200X (0.4%); Stevia Rebaudioside A (0.4%); and MagnaSweet ® (0.5%) | Vanillin (0.13%) and Ethanol (0.3%) |
| 8 | 21 | Kollidon 90F (1.5%) | Thaumatin T200X (0.4%); Stevia Rebaudioside A (0.4%); and MagnaSweet ® (0.5%) | Vanillin (0.13%) and Ethanol (0.3%) |
| 9 | 31 | Kollidon 90F (1.5%) | Thaumatin T200X (0.7%); Stevia Rebaudioside A (0.7%); and MagnaSweet ® (0.5%) | Ethyl Vanillin (0.13%) and Ethanol (0.3%) |
| 10 | 41 | Kollidon 90F (1.5%) | Thaumatin T200X (0.7%); Stevia Rebaudioside A (0.7%); and MagnaSweet ® (0.5%) | Ethyl Vanillin (0.13%) and Ethanol (0.3%) |
| 11 | 21 | Polyvinylpyrrolidone K-90 (1.5%) | Thaumatin T200X (0.4%); Stevia Rebaudioside A (0.4%); and MagnaSweet ® (0.5%) | Vanilla (0.4%) and water |
| 12 | 21 | Polyvinylpyrrolidone K-90 (1.5%) | Sucralose (0.5%) and MagnaSweet ® (0.3%) | Vanilla (0.25%) and water |

TABLE 3

Some variations of Formulation Number 9

| Material* | 9 | 9A | 9B | 9C | 9D | 9E |
|---|---|---|---|---|---|---|
| Capromorelin | 3.1 | 2.1 | 2.1 | 2.1 | 2.1 | 2.1 |
| Methyl 4-hydoxybenozate sodium salt | 0.045 | 0.132 | 0.132 | 0.132 | 0.132 | — |
| Propyl 4-hydroxy benzoate sodium salt | 0.005 | 0.018 | 0.018 | 0.018 | 0.018 | — |
| Sodium benzoate | — | — | — | — | — | 0.5 |
| Citric Acid (Anhydrous) | 0.7 | 0.7 | 1.2 | 1.2 | 1.2 | 1.2 |
| Sodium citrate | 0.5 | 0.5 | — | — | — | — |
| Sodium chloride | 0.7 | 0.7 | 0.7 | 0.7 | 0.7 | 0.7 |
| Sorbitol (70%) | 30 | — | — | — | — | — |
| Maltitol | 25 | 55 | 55 | 60 | 55 | 55 |
| Glycerol anhydrous | 20 | 20 | 20 | 20 | 20 | 20 |
| Polyvinyl-pyrrolidone | 1.5 | 1.5 | 1.5 | — | 1.5 | 1.5 |
| Vanillin | 0.2 | 0.2 | 0.2 | 0.2 | 0.2 | 0.2 |
| Ethanol | 0.5 | 0.5 | 0.5 | 0.5 | — | 0.5 |
| MagnaSweet ® | 0.5 | 2.0 | 2.0 | 2.0 | 2.5 | 2.0 |
| Thaumatin T200X | 0.6 | — | — | — | — | — |
| Rebaudiside A | 0.7 | — | — | — | — | — |
| Purified Water | q.s. | q.s. | q.s. | q.s. | q.s. | q.s. |

*Each material is listed as percent weight per volume to the total composition. Sorbitol and maltitol are interchangeable in the formulations.

TABLE 4

Some variations of Formulation Numbers 4 and 6.

| Material* | Formulation Number | | | |
|---|---|---|---|---|
| | 4 | 4A | 6 | 6A |
| Capromorelin | 2.1 | 2.1 | 2.1 | 2.1 |
| Methyl 4-hydoxybenozate sodium salt | 0.132 | 0.132 | 0.132 | 0.132 |
| Propyl 4-hydroxy benzoate sodium salt | 0.018 | 0.018 | 0.018 | 0.018 |
| Citric Acid (Anhydrous) | 1.0 | 1.0 | 0.4 | 0.4 |
| Sodium chloride | 0.7 | 0.7 | 1.0 | 1.0 |
| Maltitol | 55 | 55 | 55 | 55 |
| Glycerol anhydrous | 20 | 20 | 20 | 20 |
| Polyvinylpyrrolidone | 1.5 | 1.5 | 1.5 | 1.5 |
| Vanillin | 0.2 | 0.2 | 0.2 | 0.2 |
| MagnaSweet ® | 2.0 | 0.5 | 1.0 | 0.3 |
| Sucralose | — | — | 1.0 | 0.5 |
| Purified Water | q.s. | q.s. | q.s. | q.s. |

*Each material is listed as percent weight per volume to the total composition. Sorbitol and maltitol are interchangeable in the formulations.

The compositions can be used in conjunction with another treatment regimen that may induce weight loss.

For example, the compositions can be administered to animals (e.g., companion animals and/or livestock) as a part of a chemotherapeutic or radiation treatment regimen. One skilled in the art will recognize that chemotherapeutic or radiation treatment regimens may cause significant loss of appetite, weight loss, wasting, muscle loss, cachexia (such as cardiac cachexia), or other negative side effects that can be at least partially improved or abrogated by additional food consumption and/or increases in lean muscle mass. Accordingly, administration of therapeutically effective amounts of the compositions comprising capromorelin can induce food intake, thereby leading to weight gain and increased lean muscle mass. As a result, the animals can have more energy for activities and coping with the treatment regimens.

Moreover, the compositions can be administered to animals suffering from other conditions requiring unappetizing food. For example, some animals diagnosed with chronic kidney disease (CDK) are placed on a specialized diet to improve this condition. However, some animals do not find the specialized diet food to be appetizing, and, as a result, do not consume enough of the specialized diet food for treatment of the chronic kidney disease or for sustenance. Accordingly, some animals can receive therapeutically effective amounts of the weight-gaining composition comprising capromorelin to stimulate hunger and induce consumption of the specialized diet food, especially for treatment periods of at least 8 days, for example of at least 30 days, at least 45 days, or at least 90 days. As a result, the chronic kidney disease can be better controlled by the specialized diet food and the animal can consume sufficient calories for a pleasant existence.

In cats suffering from CKD, weight loss is common. Anorexia (complete loss of appetite) can occur in cats with CKD, especially as the disease progresses, but more common are hyporexia (decreased appetite) or dysrexia (changes in food preferences or in patterns of food intake). Any alteration in appetite can contribute to weight and muscle loss. In humans, weight and muscle loss in CKD patients also negatively impact strength and immune function, and can contribute to morbidity and mortality in this population. Because euthanasia is an option for cat owners, reduced or altered appetite can contribute indirectly to mortality because appetite is a way owners assess their animal's quality of life and so is a major factor in the euthanasia decision. Conversely, increased appetite and maintained or increased bodyweight is a positive sign for veterinarians and owners. Increased appetite may enhance adherence to a veterinary diet designed for cats with CKD, which can reduce renal secondary hyperparathyroidism, minimize uremic episodes and CKD-related mortality, and increase survival.

Although weight loss is a common clinical sign in cats with CKD, the details and patterns of weight loss are rarely studied. One retrospective case-control study of cats with CKD compared to an age matched control group (n=1230/group) showed that cats with CKD were more likely to be classified as thin compared to controls. In the same study, reduced appetite also was significantly more common in the cats with CKD both before and at CKD diagnosis, compared to controls. In this population of cats, bodyweight was significantly lower in the cats with CKD (median=4.0, range 1.6-11.7 kg) compared to controls (median=4.8, range 1.4-13.2 kg) at the time of diagnosis but, more importantly, the cats with CKD also had lost significantly more weight in the 6-12 months before diagnosis. Cats with CKD had lost a median of 10.8% of bodyweight, while the healthy controls had a median weight loss of only 2.1% (p<0.001). The mean weight loss in CKD cats was about 5 times that of controls on a percentage weight loss basis, suggesting that "the greater loss of weight in the case group was likely associated more with the development of CKD rather than simply the effect of aging."

While these data support the common notion that cats with CKD are thin and have already lost bodyweight at diagnosis of CKD, the time course and progression of weight loss before and after diagnosis have not been thoroughly evaluated in any published research. Recently, data collected from the medical records of a large group of cats with CKD indicate that weight loss begins long before CKD diagnosis and progresses rapidly after diagnosis. Cats with CKD for which International Renal Interest Group Stage (IRIS) was available were eligible to be included in the analysis. Only those cats with age, date of CKD diagnosis, and bodyweight measurements available in the 3 years before and after diagnosis were included in the analysis. A total of 569 cats (55.5% spayed females and 44.5% castrated males) with a mean age at diagnosis of 14.5±2.8 years, were evaluated. Cats were categorized at diagnosis as IRIS Stage 1 [n=34 (6%)], Stage 2 [n=345 (61%)], Stage 3 [n=141 (25%)], and Stage 4 [n=49 (9%)]. Median body weight at diagnosis was 4.2 kg (range, 1.6-9.9 kg).

Cats had lost a median of 8.9% of bodyweight in the 12 months before diagnosis, and weight loss was already present during the 3 years before CKD diagnosis and increased progressively over time. The rate of weight loss was even higher in older cats with CKD. Cats in this analysis below the median bodyweight (4.2 kg) at diagnosis had a significantly shorter survival time compared to cats with a bodyweight ≥4.2 kg at diagnosis (p<0.0001). As in a study of cats with congestive heart failure, there was a U-shaped association of survival with bodyweight in this population of cats with CKD; that is, survival was shortest for cats in the lowest and highest body weight categories, with the longest survival for cats with moderate bodyweights.

Thus, weight loss can be detected at least three years before the diagnosis of CKD in cats and increases progressively over time. Cats with a lower bodyweight had a shorter survival time, meaning that careful monitoring may detect weight loss and possibly CKD at an earlier stage. This would allow for earlier intervention in these cats that already have weight loss, to encourage cats to eat, to increase body weight to normal levels, and to potentially benefit feline health.

The compositions can be used to treat a general state of weight loss. For example, some animals, for unknown reasons, experience weight loss, which, as previously mentioned, can lead to wasting, cachexia (such as cardiac cachexia), lethargy, and other unpleasant results. After diagnosis of weight loss by one skilled in the art, such as a veterinarian, the animals can receive one or more therapeutically effective doses of the composition comprising capromorelin to increase food consumption and lean muscle mass. As result, the companion animals can experience healthy weight gain leading to an improved quality of life.

The composition can be used to increase lean muscle mass. For example, it can be desirous to increase the lean muscle mass in some animals (e.g., livestock such as bovine or porcine animals). Accordingly, the composition can be administered in a therapeutically effective amount in one or more doses to increase lean muscle mass without the need to treat weight loss.

The treatment regimen of the inappetance-controlling composition can be at least partially adjusted during the course of treatment. For example, after the animal is diagnosed as experiencing weight loss (e.g., regardless of cause), an amount of the composition believed to be therapeutically effective can be administered to the animal (e.g., orally, intravenously, etc.). After a pre-determined time period, (e.g., about eight hours after the first administration of the composition and about seven days later), a technician, a veterinarian, or any other suitable individual can extract a sample (e.g., a serum sample) from the animal to measure amounts of one or more markers within the sample.

The samples can be taken any other suitable time points known to those skilled in the art that would be appropriate for measuring the one or more markers of drug effect. For example, the markers can comprise at least one of IGF-1, GH, capromorelin, and/or cortisol. As a result of knowing the amounts of one or more of these markers, the dose of the composition can be adjusted in light of the amounts of the markers within the sample. Accordingly, the effectiveness of composition can be determined and adjusted during the course of treatment. For example, if the amount of IGF-1 within the sample is not great enough, the dose of the composition can be increased in either concentration of capromorelin or amount of capromorelin administered to the companion animal. Conversely, if the amount of cortisol within the sample is too great, which can lead to increased adipose deposition, the dose interval of the composition can be decreased in either concentration of capromorelin or amount of capromorelin administered to the companion animal.

The above treatment regimen can be carried out without extracting a blood sample. For example, after administering one or more the therapeutically effective doses to the animal (e.g., after about seven days of receiving treatment), other markers of weight loss can be measured to assess the effectiveness of the treatment regimen. These markers can include change in bodyweight (e.g., continued weight loss, weight gain, weight loss stabilization), a change in food intake (e.g., increase in food intake relative to the pre-treatment time period), and/or a measurement of a change in lean muscle (e.g., scoring a value of the lean muscle index of the animal to assess lean muscle growth). As a result, the animal does not experience the invasive extraction of a blood sample and the individuals monitoring the treatment regimen can accordingly adjust the dose of the treatment regimen.

Although the invention described herein is susceptible to various modifications and alternative iterations, specific embodiments thereof have been described in greater detail above. It should be understood, however, that the detailed description of the spot-on composition is not intended to limit the invention to the specific embodiments disclosed. Rather, it should be understood that the invention is intended to cover all modifications, equivalents, and alternatives falling within the spirit and scope of the invention as defined by the claim language.

Definitions

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "animal" designates non-human animals, such as "livestock" and "companion animals."

As used herein, the term "livestock" includes cattle, sheep, pigs, poultry (e.g., chickens, turkeys, quail, etc.) goats, llamas, and other similar animals.

As used herein, the term "h" designates hours.

As used herein, the term "composition" applies to any solid object, semi-solid, or liquid composition designed to contain a specific pre-determined amount (dose) of a certain ingredient, for example, an active pharmaceutical ingredient, as previously mentioned and as discussed below. Suitable compositions may be pharmaceutical drug delivery systems, including those for oral administration, buccal administration, rectal administration, topical or mucosal administration, or subcutaneous implants, or other implanted drug delivery systems; or compositions for delivery minerals, vitamins and other nutraceuticals, oral care agents, flavorants, flavor-masking agents, and the like. The compositions can be generally liquid, however they may contain solid or semi-solid components. Generally, the dosage form is an orally administered system for delivering a pharmaceutical active ingredient to the alimentary canal of a companion animal.

As used herein, the term "mg/kg" designates milligrams of composition per kilogram of bodyweight.

As used herein, the term "treatment" or "treating" of a condition, such as chronic inappetance or weight loss, includes inhibiting an existing condition or arresting its development; or ameliorating or causing regression of the condition. The term "preventing" or "prevention" of a condition, such as chronic inappetance, weight loss, or cachexia, includes substantially blocking or inhibiting the development or growth of a condition before it starts.

As used herein, the term "animal" refers to a mammal, specifically a companion animal, including but not limited to dogs, cats, rabbits, ferrets, horses, and hamsters.

The companion animal may be a dog. The companion animal may be a cat. The companion animal may be a horse.

As used herein, the phrase "therapeutically effective amount" refers to an amount effective, at dosages and for periods of time necessary, to achieve the desired therapeutic result. A therapeutically effective amount of capromorelin may be determined by a person skilled in the art (e.g., a veterinarian) and may vary according to factors such as the clinical state, age, sex, and weight of the companion animal, bioavailability of capromorelin, and the ability of the active agent(s) to elicit a desired response in the companion animal. A therapeutically effective amount is also one in which any toxic or detrimental effects of the active agent(s), are outweighed by the therapeutically beneficial effects. A therapeutically effective amount also encompasses an amount that is effective, at dosages and for periods of time necessary, to achieve the desired result (e.g., weight gain through the addition of lean muscle mass).

As used herein, the term "q.s." means to add a quantity (e.g., volume or mass) of an ingredient until the final amount (e.g., volume or mass) is reached.

As used herein, the term "w/v" designates a concentration of a substance as measured in weight of the substance per volume of a solution or composition.

The following examples are intended to further illustrate and explain the present disclosure. The disclosure, therefore, should not be limited to any of the details in these examples.

EXAMPLES

Example 1—Safety of Capromorelin Administered Daily to Beagle Dogs for One Year

This study evaluated the safety of capromorelin in dogs. Thirty-two Beagle dogs were randomly assigned to four groups (n=4/sex/group) and received 0 mg/kg, 0.39 mg/kg, 9.2 mg/kg, or 52.4 mg/kg capromorelin (with the dose calculated per the tartrate salt) once daily by oral gavage for 12 consecutive months. Safety parameters were evaluated including clinical signs, food consumption, bodyweight, clinical pathology, urinalysis, ophthalmology, electrocardiogram and vital signs. Capromorelin, GH and IGF-1 were measured in plasma samples collected at various time points during the study. At the end of the dosing period, dogs were humanely euthanized and necropsied. Selected organs were weighed and tissue samples collected and processed for microscopic examination.

Capromorelin at daily doses up to 52.4 mg/kg (approximately 17.5 times the active ingredient concentration in the proposed clinical dose for dogs) for 12 months resulted in minimal toxicity with no negative effects on food consumption, bodyweight, ophthalmic exams, vital signs or gross pathology. Clinical signs related to capromorelin were limited to salivation and loose stool noted sporadically during the study. Occasional episodes of emesis were observed and considered unrelated to treatment. The higher dose treatments were associated with an increased incidence of reddening/swollen paws. One dog in the 52.4 mg/kg group died when capromorelin was accidentally delivered into the respiratory tract during gavage as confirmed by necropsy.

Electrocardiogram data indicated slight increases in the pressure rate quotient (PRQ) interval in the 52.4 mg/kg and the 9.2 mg/kg groups 1 to 2 hours following dosing. However, no histological lesions were observed in the heart. In general, clinical pathology and urinalysis parameters were within normal ranges or lacked a consistent dose/time relationship. However, the slight deceases in red blood cells, hemoglobin and hematocrit did not appear to be clinically significant in the 52.4 mg/kg group.

Cholesterol, high-density lipoprotein (HDL) and alkaline phosphatase serum levels were statistically significantly increased in the 52.4 mg/kg group compared to placebo and individual animal values tended to be at the high end or slightly above the normal reference range. Increased absolute liver weights in dogs treated with the 52.4 mg/kg dose of capromorelin were noted. A slight increase in hepatocellular cytoplasmic vacuolation was seen in all capromorelin treated groups. Capromorelin plasma levels increased with increasing dose, were similar on Days 90, 181, and 349 indicating no accumulation of drug and there were no gender-related differences. GH plasma levels increased modestly as expected on Days 1, 170 and 351 following capromorelin treatment. The GH response was controlled by a physiological negative feedback so that the magnitude of the GH response to capromorelin treatment lessened over time. IGF-1 plasma levels increased following capromorelin treatment and increased levels were sustained over time as evidenced in plasma collected on Days −1, 1, 7, 14, 21, 28, 62, 121, 170, and 351.

The results of this study demonstrated that capromorelin was well-tolerated in dogs dosed up to 52.4 mg/kg for 12 months. Further, this study indicates an expected wide safety margin for capromorelin as the high dose is about 17.5 times the proposed clinical dose.

Example 2—Capromorelin Efficacy in Cats for 21 Days

Thirty-two cats (16 neutered males, 16 females) were divided into 4 treatment groups including 4 animals of each sex per group. The cats were acclimated to the study environment for 10 days prior to study start. All cats were orally dosed with placebo (Group 1) or capromorelin (30 mg/ml oral solution, Formulation 9 as described above) at 1 mg/kg (Group 2), 2 mg/kg (Group 3) or 3 mg/kg (Group 4), for 21 days, with dosing starting on Day 1. Physical examinations were performed on Day −10 and general health observations made daily. Body weights were evaluated on Days −10, −8, −1, 1, 8, 15 and 22 days. Cats were fed about 1 hour after dosing. Commercial dry cat food (300 g) was provided for 5 hours and then removed and the amount of food consumed (g) calculated per cat. On Days 1, 14 and 21, blood samples were collected prior to daily dose administration and at 8 hours post-dose and serum processed for measurement of IGF-1 levels.

On Day 12, two study animals (one male each from Groups 1 and 4) were removed for reasons unrelated to the study and were not included in the data analysis. Cat 4M4 in the 3 mg/kg group lost significant weight during the first 8 days of treatment—then rebounded and began to gain the weight back. Statistical analysis for weight gain was completed with and without this cat's (4M4) data included.

All treatment groups were observed to have increased mean food consumption from the baseline period (average of Days −3, −2 and −1) compared to the study period (average of Day 1 to Day 21). Referring to FIG. 1, the placebo cats (Group 1) had a mean food intake increase of 10.83% over baseline, while the three capromorelin groups (Groups 2, 3 and 4) had mean food intake increases over baseline of 25.32%, 45.67% and 29.59%, respectively with only Group 3 showing a statistically significant (p<0.01) increase in food consumption when compared to the placebo group.

For the food consumption analysis of the average of values, the overall treatment effect for the intervals from Day 1 through Day 21 (p=0.0066), Day 1 through Day 7 (p=0.0004) and Day 8 through Day 14 (p=0.0164) were found to be statistically significant. For the interval from Day 1 through Day 7, pairwise comparisons were found to be statistically significantly different for each active group when compared to the placebo group (1 mg/kg group (p=0.0418); 2 mg/kg group (p=0.0002); and 3 mg/kg group (p=0.0022)). For the interval from Day 1 through Day 21, only the 2 mg/kg group (mean=45.67%, p=0.0019) was found to be statistically significantly different from placebo (mean=10.83%). The 2 mg/kg group (mean=54.42%, p=0.0052) was also found to be statistically significantly different from placebo for the interval from Day 8 through Day 14.

Figure 2:
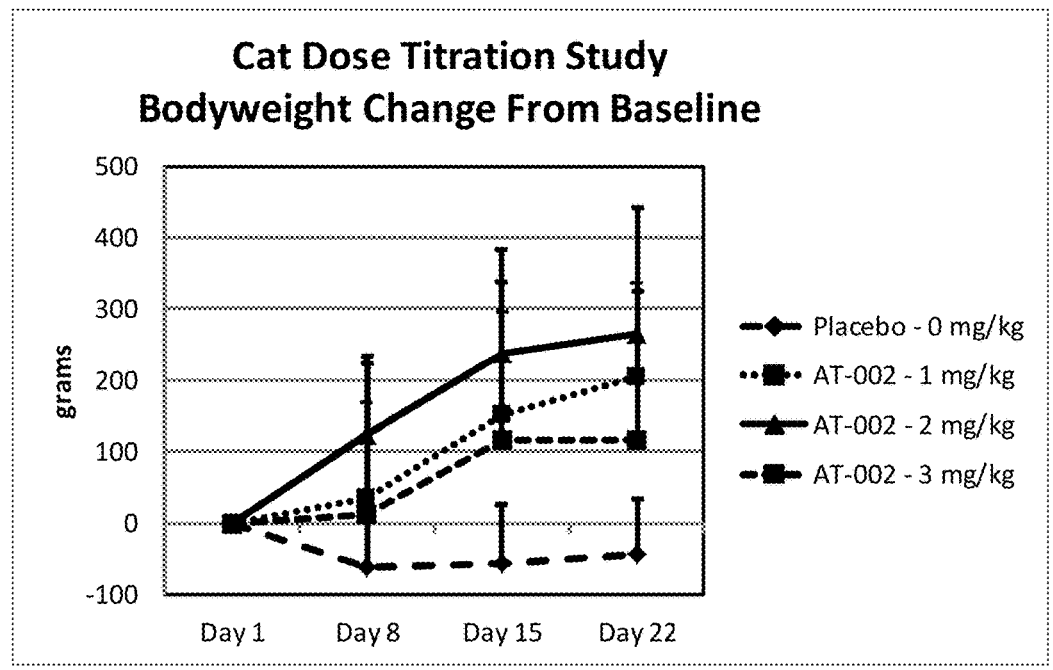
FIG. 2 depicts bodyweight change from baseline in grams over time for the cat dose titration study, as described in Example 2. The bodyweight changes are compared for placebo and capromorelin (AT-002) doses at 1 mg/kg, 2 mg/kg, and 3 mg/kg.
Figure 3:
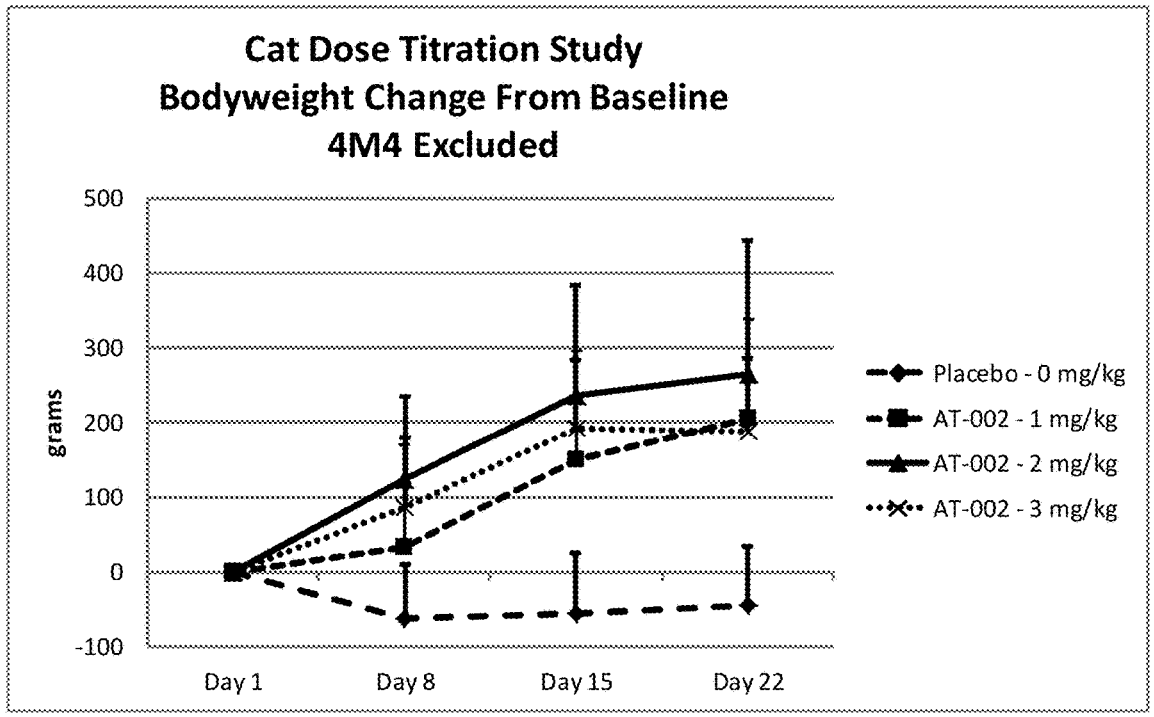
FIG. 3 depicts bodyweight change from baseline in grams over time for the cat dose titration study, as described in Example 2 and as shown in FIG. 2, but with cat 4M4 excluded from the analysis.
Figure 4:
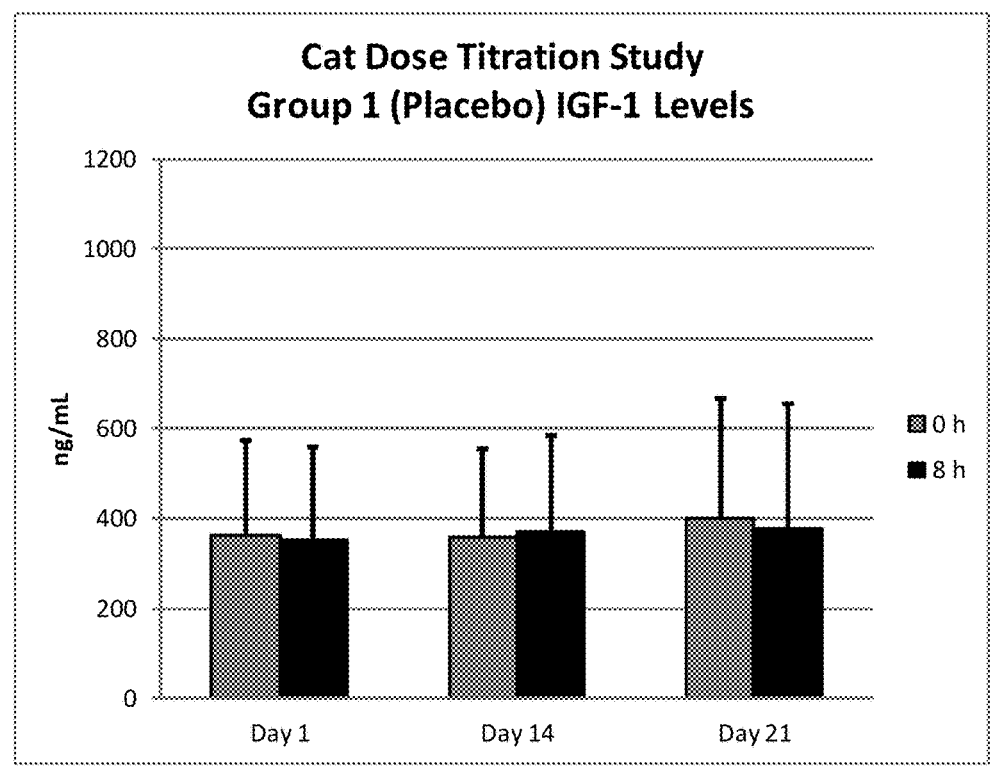
FIG. 4 depicts Group 1 (placebo) insulin-like growth factor 1 (IGF-1) levels in ng/mL at hours 0 and 8 for Days 1, 14, and 21 in the cat dose titration study, as described in Example 2.
Figure 5:
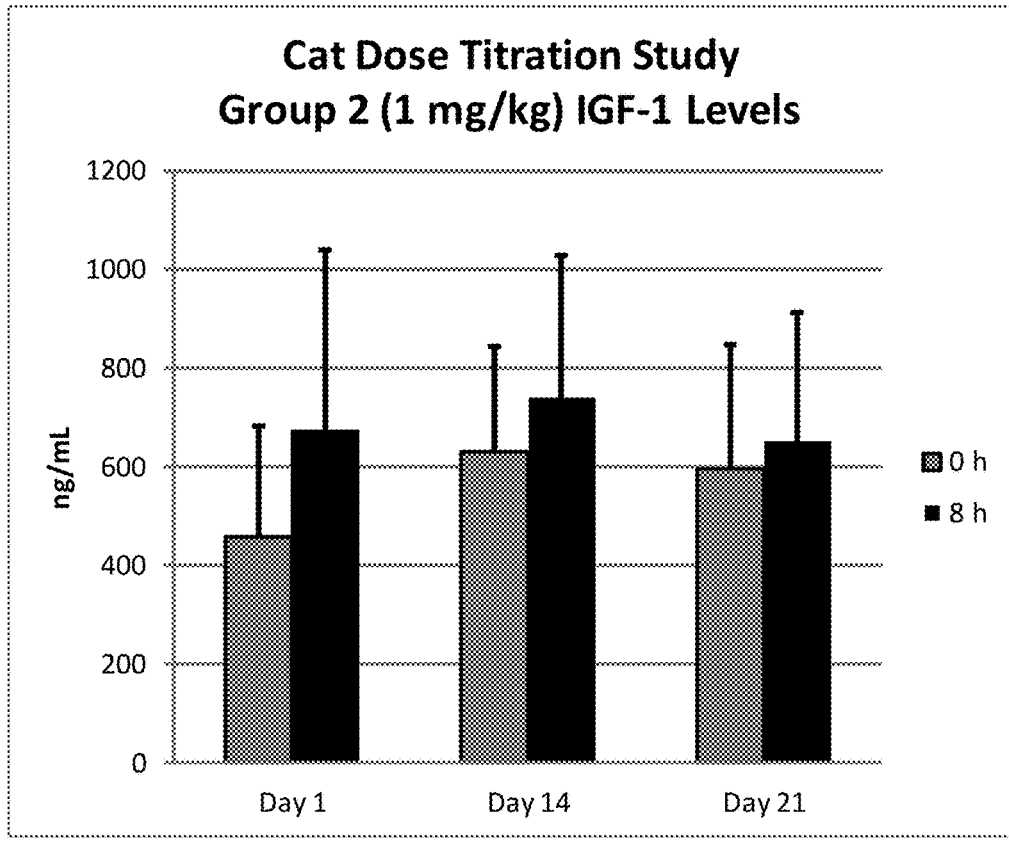
FIG. 5 depicts Group 2 (1 mg/kg capromorelin) insulin-like growth factor 1 (IGF-1) levels in ng/mL at hours 0 and 8 for Days 1, 14, and 21 in the cat dose titration study, as described in Example 2.
Figure 6:
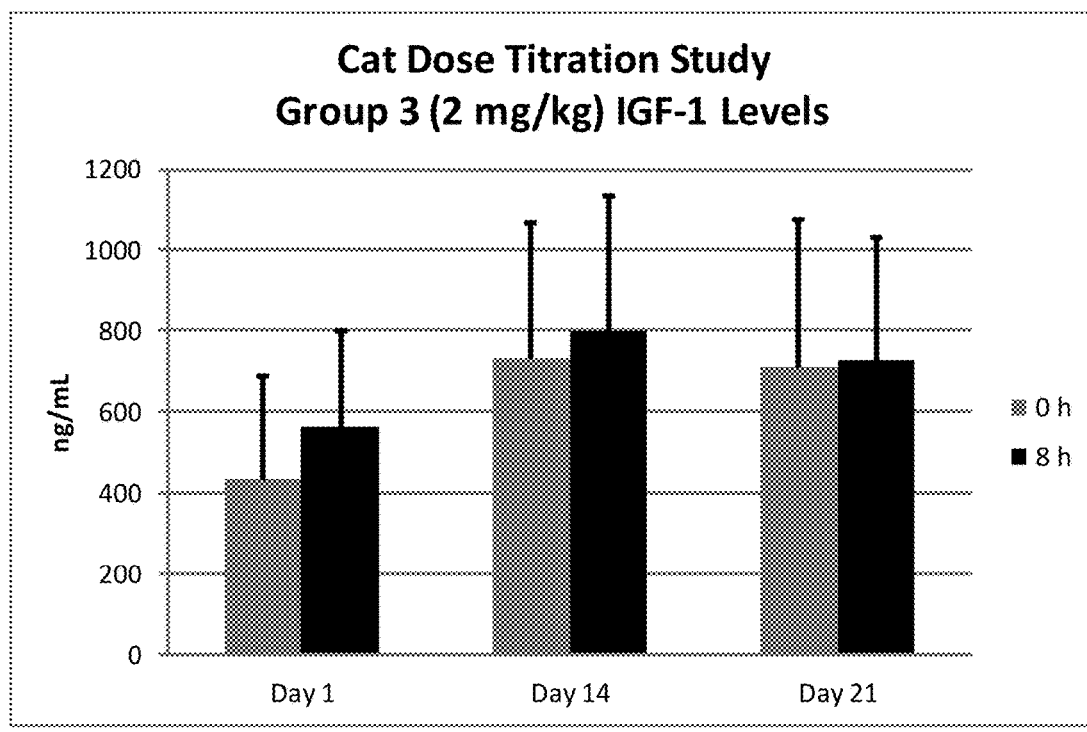
FIG. 6 depicts Group 3 (2 mg/kg capromorelin) insulin-like growth factor 1 (IGF-1) levels in ng/mL at hours 0 and 8 for Days 1, 14, and 21 in the cat dose titration study, as described in Example 2.
Figure 7:
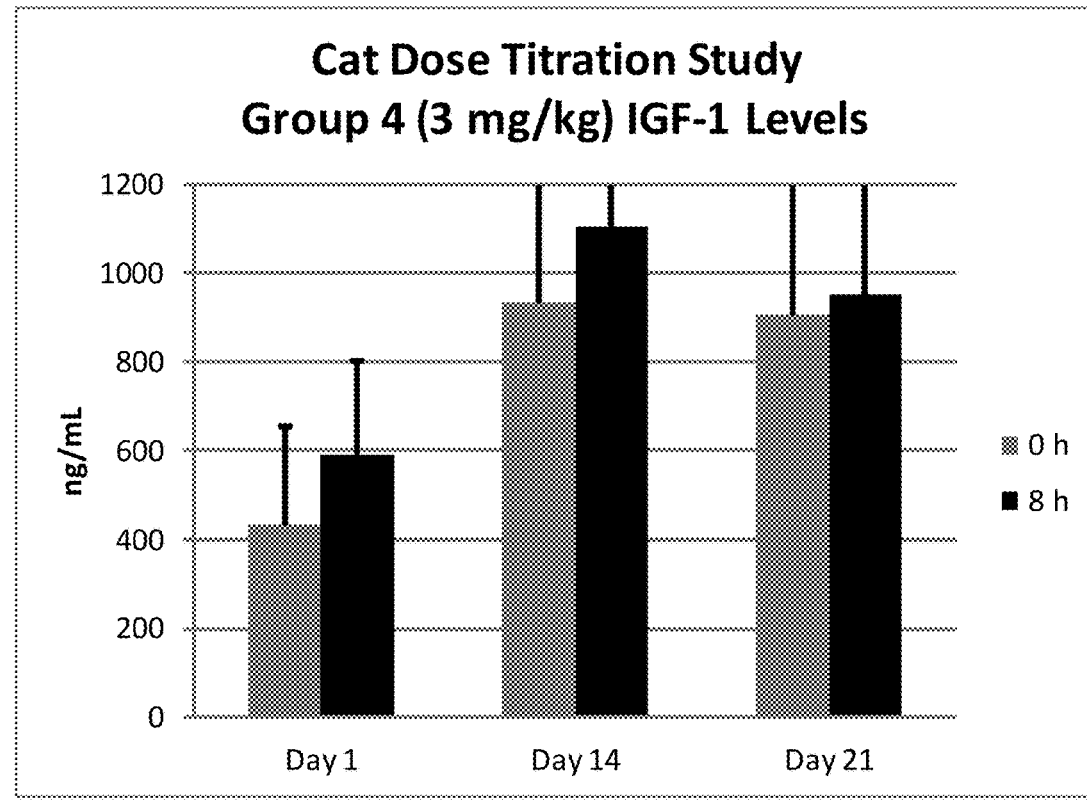
FIG. 7 depicts Group 4 (3 mg/kg capromorelin) insulin-like growth factor 1 (IGF-1) levels in ng/mL at hours 0 and 8 for Days 1, 14, and 21 in the cat dose titration study, as described in Example 2.

Referring to FIGS. 2 and 3, mean bodyweights for the capromorelin treatment groups increased during the 21-day exposure period. Groups 2, 3 and 4 had increases of 5.41%, 6.61% and 3.92% respectively whereas the placebo group lost a small amount of weight (minus 1.11%). Statistically significant differences from placebo (p<0.05) in mean percent bodyweight change were observed for Group 3 at all three time points measured with increases of 3.23%, 5.97% and 6.61% on Days 8, 15 and 22, respectively. Surprisingly, Group 2 had mean percent bodyweight changes that were statistically significantly increased (p<0.05) when compared to placebo at Day 15 (4.24%) and Day 22 (5.41%), but not at Day 8.

The interaction of treatment by sex was not statistically significant (p>0.05) for either food consumption or weight gain, indicating that the effect of treatment was similar in male and female cats.

Referring to FIGS. 4-7, in Group 1, IGF-1 levels remained at baseline levels throughout the study. On Day 1, group mean serum IGF-1 levels increased from 0 to 8-hours post-dose by 46.69%, 29.38% and 36.77% for Groups 2, 3 and 4, respectively. On Day 14, IGF-1 levels were sustained at a higher level at hour 0. Therefore, the group mean increase in serum IGF-1 levels was lessened from 0 to 8-hours post-dose (17.27%, 9.00% and 18.56% for Groups 2, 3 and 4, respectively). On Day 21, the trend of a smaller IGF-1 response continued as group mean IGF-1 levels increased from 0 to 8-hours post-dose by 9.81%, 2.68% and 5.17% for Groups 2, 3 and 4, respectively. The smaller increases of IGF-1 levels following capromorelin treatment on Day 14 and Day 21 were due to the fact that by Day 14 there was a sustained elevation in IGF-1 resulting from repeated daily capromorelin treatment.

In conclusion, capromorelin increased food intake, promoted weight gain and caused sustained increases in IGF-1 in laboratory cats.

Example 3—Safety of Daily Capromorelin in Cats for 91 Days at an Oral Dose of 6 Mg/Kg This controlled study included two treatment groups with 4 adult cats receiving placebo (Group 1) and 8 adult cats receiving capromorelin (Formulation #9, as described above) (Group 2) for 91 consecutive days. All cats were offered food daily for a 6-hour period following an 11-day acclimation phase. All cats were weighed on Days −11, −1, 1, 14, 30, 59, 75, and 91. On Days 1 through 91, animals were orally administered capromorelin once daily via syringe at dose levels of 0 or 6 mg/kg. At one hour post-dose, all cats were offered food for a 6-hour period. Variables of interest included weight gain/loss, food consumption, clinical pathology, and serum analysis of IGF-1 and GH.

On Days 1, 30, 59, and 91, blood samples were collected prior to daily dose administration and at 8 hours post-dose and processed to serum for analysis of IGF-1 and GH levels. Hematology parameters included white blood count (WBC), hemoglobin (HgB), red blood count (RBC), platelet count (PLT), platelet morphology, hematocrit (HCT), mean corpuscular volume (MCV), mean corpuscular hemoglobin (MCH), WBC differential, RBC and WBC morphology, mean corpuscular hemoglobin concentration (MCHC), reticulocytes, and blood smear. Serum chemistry parameters measured included albumin (ALB), creatine kinase (CK), albumin/globulin ratio (A\G), globulin (GLOB), alkaline phosphatase (ALP), glucose (GLU), fructosamine, alanine aminotransferase (ALT), blood urea nitrogen (BUN), phosphorus (PHOS), calcium (Ca), potassium (K), chloride (Cl), sodium (Na), cholesterol (CHOL), total protein (TP), creatinine (CRE), total bilirubin (TBIL), BUN/creatinine ratio, and sodium/potassium ratio.

Urine samples were collected via cystocentesis and/or by collection in pans/trays from all cats for urinalysis. Before blood collection, all animals were fasted at least 8 hours. Urinalysis parameters measured included specific gravity (SG), pH (PH), color (COL), clarity (CLAR), blood (BLO), protein (UPRO), bilirubin (UBIL), glucose (UGLU), ketones (KET), and the microscopic examination of the sediments for RBC/hpf, WBC/hpf, bacteria (BACT), epithelial cells, mucus, casts, and crystals.

During the study, the most common clinical observations were hypersalivation (ptyalism), lip smacking, emesis, and head shaking. These findings were seen immediately post-dose and usually resolved within five minutes. No other abnormal general health or clinical observations were observed.

In general, all animals maintained or increased body-weight during the exposure period (bodyweight calculation from Day 1 to Day 91). Mean values for male animals in Group 2 (capromorelin) moderately increased in body-weight while male animals in Group 1 (placebo) remained relatively unchanged. Mean values for female animals in Group 2 slightly increased in bodyweight as compared to female animals in Group 1.

Figure 8:
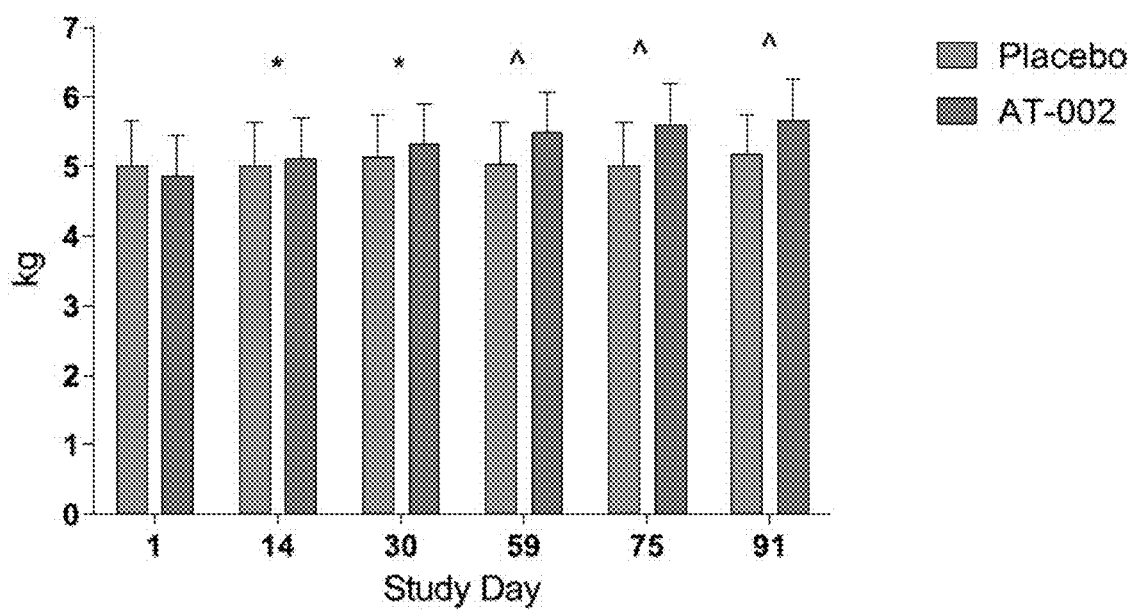
FIG. 8 depicts mean bodyweight over time for placebo- and capromorelin (AT-002)-treated cats, as described in Example 3. Treatment by study day interaction was statistically significant ($p<0.0001$). The asterisk (*) indicates that the change from baseline was significantly different for capromorelin vs. placebo ($p<0.01$). The carat (^) indicates that the change from baseline was significantly different for capromorelin vs. placebo ($p<0.0001$).

Cats treated with capromorelin clearly gained weight (FIG. 8). Placebo control cats maintained a consistent body-weight during the study. The treatment effect and treatment by study day interaction term was found to be statistically significant (p<0.0001). The changes from baseline (Day 1) were statistically significant between treatment groups at Day 14 (p=0.0026), Day 30 (p=0.0005), Day 59 (p<0.0001), Day 75 (p<0.0001) and Day 91 (p<0.0001). The mean changes for capromorelin were 0.26, 0.46, 0.64, 0.73, and 0.80 kg at Days 14, 30, 59, 75, and 91, respectively. For placebo the mean changes were 0.00, 0.11, 0.00, 0.00, and 0.16 kg at Days 14, 30, 59, 75, and 91, respectively. For the analysis of the rate of bodyweight change, the treatment effect was statistically significant (p=0.0011). The mean rate of change was 0.0086 for capromorelin and was 0.0010 for the placebo group (a factor of 8.6).

Figure 9:
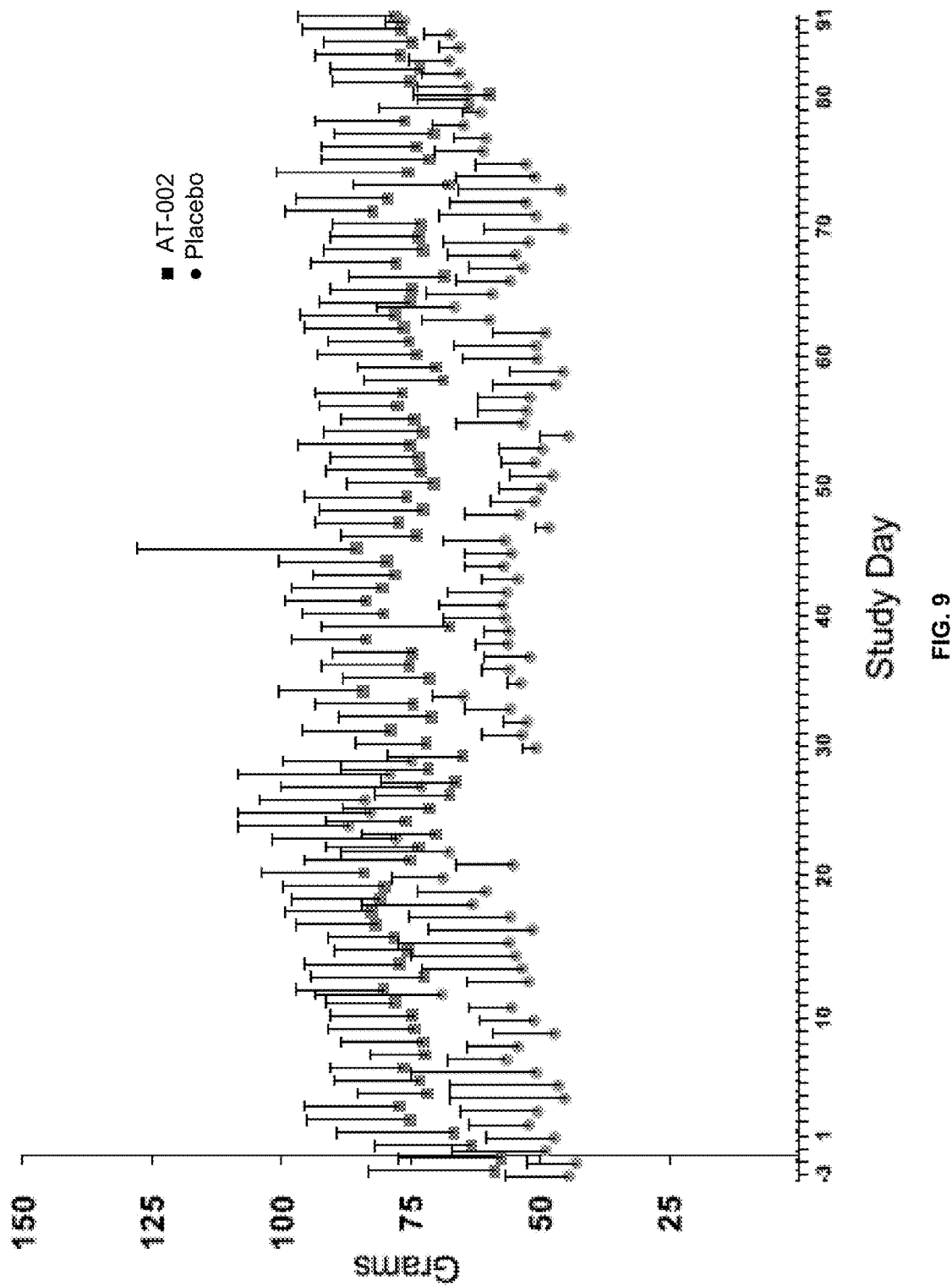
FIG. 9 depicts food consumption in grams over time for placebo- and capromorelin-treated cats, as described in Example 3.

The capromorelin treated cats had increased food consumption compared to placebo treated cats (FIG. 9, P-value=0.0909). This food consumption trend did not show strong statistical significance. Certainly, treatment with capromorelin at a dose of 6 mg/kg did not negatively affect food consumption in the cat. During the study (Days −11 through 90), food consumption was calculated daily for all animals. During the acclimation period baseline food consumption values were calculated using the average of Days −3 through −1 for all animals. For food consumption, the p-value of the treatment effect was 0.0909. (Day 83 and Day 84 were not included in the analyses because the feeding was not consistent with the other days.) The mean change from baseline was 14.95 grams for capromorelin and 11.84 grams for placebo. For the analysis of the rate of change, the p-value of the treatment effect was 0.0565. The mean rate of change was 1.2396 for capromorelin and was 0.9590 for the placebo group. A rate of one indicates that for each day, one more gram of food was consumed. Because the rate seen in capromorelin-treated cats is greater than one, for each day slightly more than one gram of food was consumed.

Figure 10:
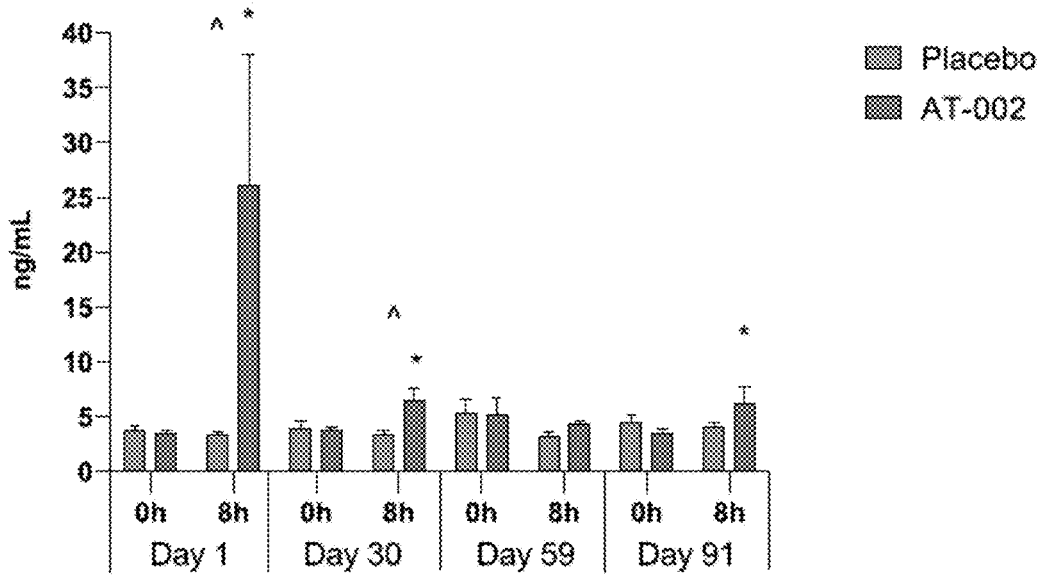
FIG. 10 depicts mean growth hormone (GH) levels in ng/mL over time for placebo- and capromorelin-treated cats, as described in Example 3. The asterisk (*) indicates that capromorelin-treated cats had significantly different GH at 0 hours vs. 8 hours ($p<0.05$). The carat (^) indicates that the change from 0 hours to 8 hours was significantly different for capromorelin vs. placebo ($p<0.05$).

Data show that in capromorelin-treated cats GH increased following treatment compared to placebo controls (FIG. 10). The increase of GH was very pronounced on the first day of capromorelin treatment. The GH increase was attenuated as daily capromorelin treatment progressed through Days 30, 59, and 91 indicating a negative feedback on the hormonal mechanism causing GH secretion.

Figure 11:
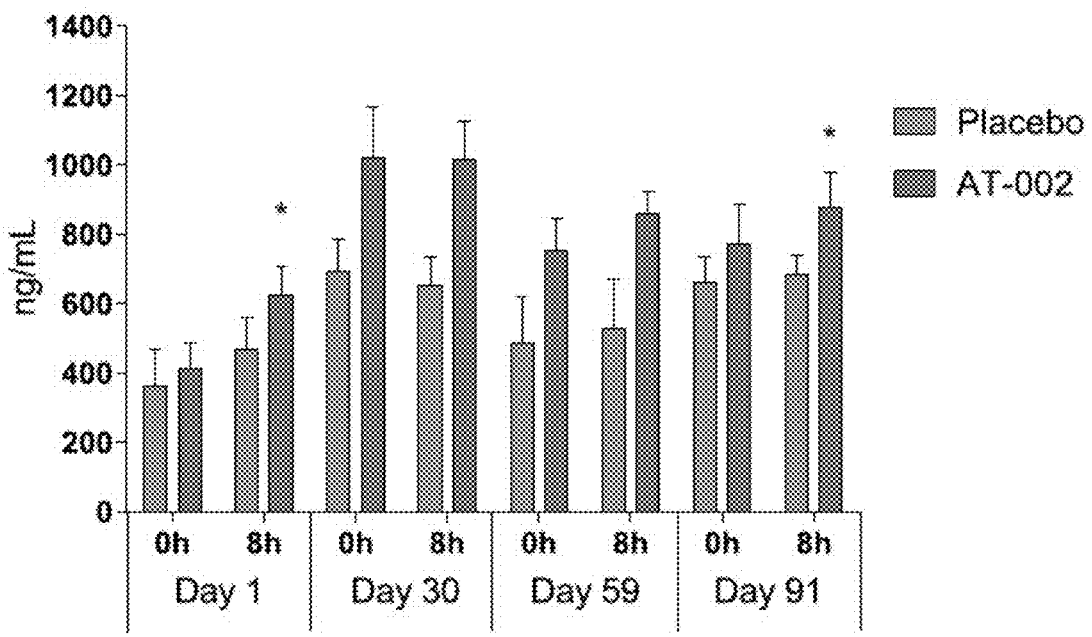
FIG. 11 depicts mean insulin-like growth factor-1 (IGF-1) levels in ng/mL over time for placebo- and capromorelin-treated cats, as described in Example 3. Treatment by study day interaction was statistically significant ($p<0.05$). The asterisk (*) indicates that capromorelin-treated cats had significantly different IGF-1 at 0 hours vs. 8 hours ($p<0.05$).

Data show that in capromorelin-treated cats IGF-1 increased following treatment compared to placebo controls (FIG. 11). The increase of IGF-1 became sustained as daily treatment of capromorelin continued. The IGF-1 sustained increase peaked at Day 30 and then decreased over time.

Figure 12:
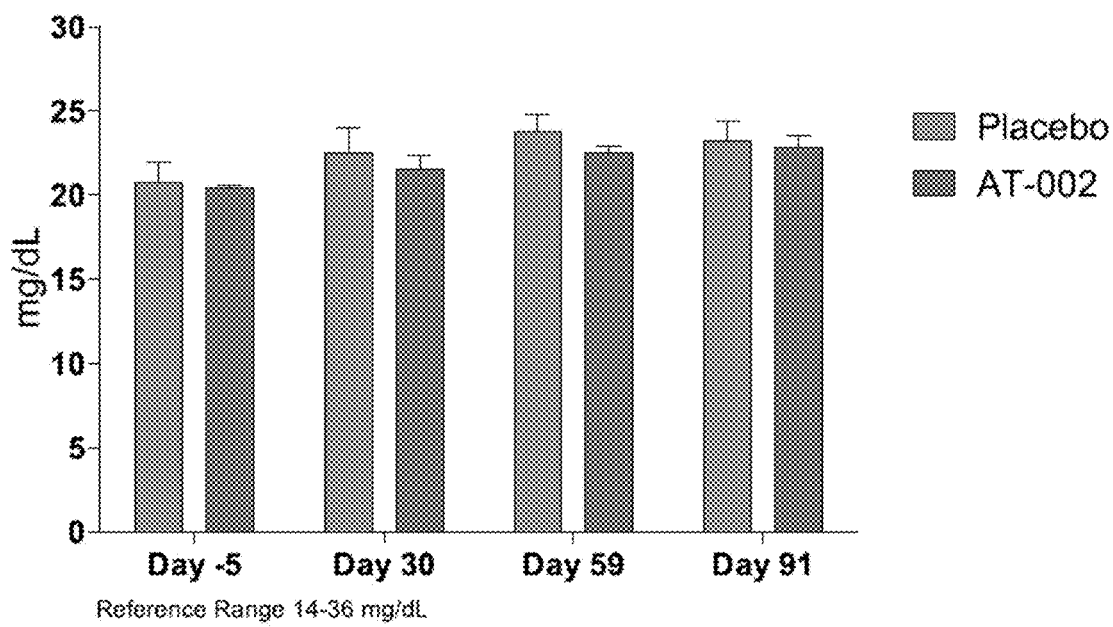
FIG. 12 depicts mean blood urea nitrogen (BUN) levels in mg/dL over time for placebo- and capromorelin-treated cats, as described in Example 3. The reference range was 14 mg/dL to 36 mg/dL.
Figure 13:
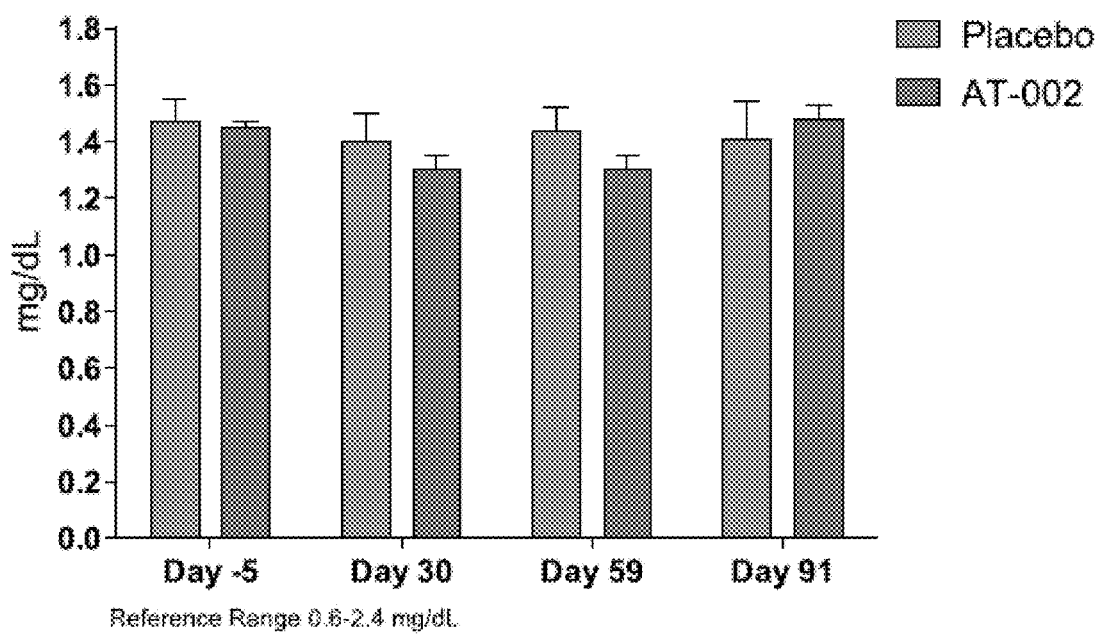
FIG. 13 depicts mean creatinine (CRE) levels over time for placebo- and capromorelin-treated cats, as described in Example 3. The reference range (normal level) was 0.6 mg/dL to 2.4 mg/dL. Treatment by study day interaction was statistically significant ($p<0.1$).

BUN levels (mg/dL) trended slightly higher in most cats from acclimation to Day 91 (FIG. 12). BUN levels were similar for control cats and capromorelin cats. All observations were within the normal reference range. Creatinine levels (mg/dL) trended flat in most cats from acclimation to Day 91 (FIG. 13). Creatinine levels were similar for control cats and capromorelin cats. All observations were within the normal reference range. Since BUN and creatinine are parameters for monitoring potential chronic kidney disease, the trends noted in this study are encouraging because they do not indicate that capromorelin-treated cats differ from placebo treated cats.

Figure 14:
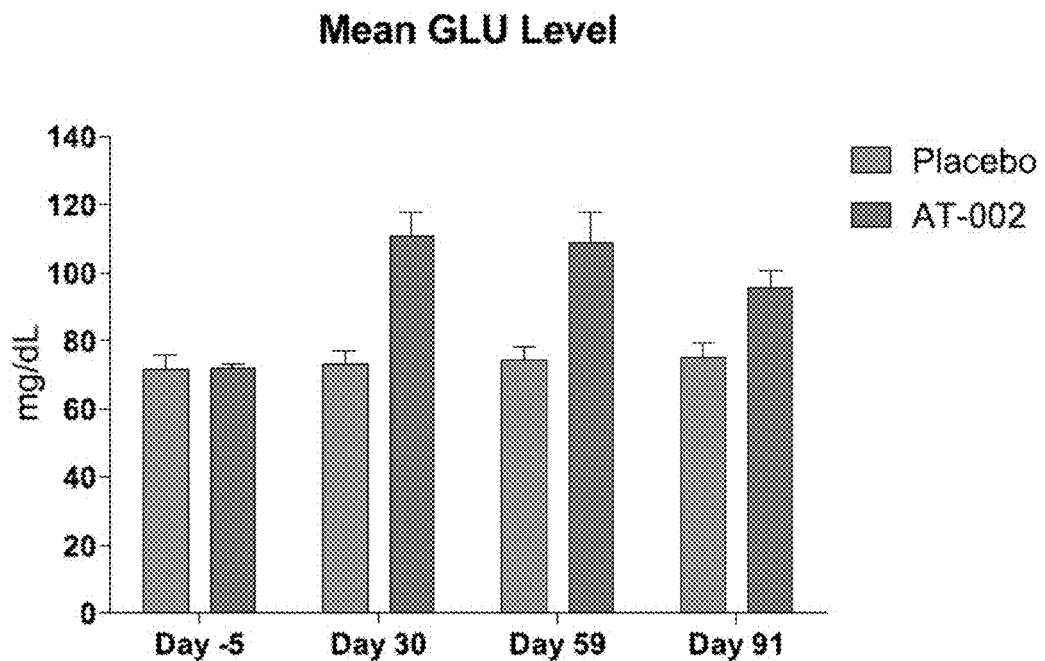
FIG. 14 depicts mean glucose (GLU) levels over time for placebo- and capromorelin-treated cats, as described in Example 3. The reference range (normal level) was 64 mg/dL to 170 mg/dL. The data indicate a statistically significant treatment effect ($p<0.1$).
Figure 15:
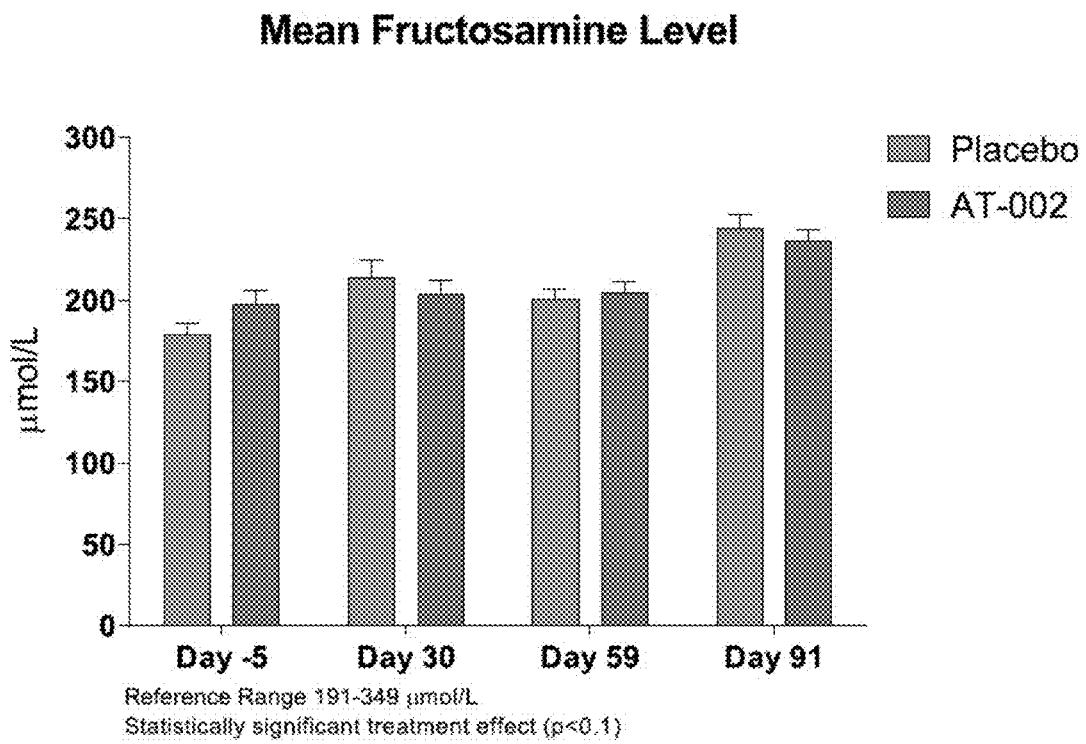
FIG. 15 depicts mean fructosamine levels over time for placebo- and capromorelin-treated cats, as described in Example 3. The reference range (normal level) was 191 μmol/L to 349 μmol/L. The data indicate a statistically significant treatment effect ($p<0.1$).

In general, the statistically significant differences for clinical pathology safety parameters were not clinically relevant. Serum glucose levels were increased in the capromorelin-group compared to the placebo group and there was an increasing trend over time (FIG. 14). No glucose values exceeded the normal reference range. Fructosamine is a parameter used in monitoring chronic hyperglycemia. There were no capromorelin-related serum fructosamine level trends (FIG. 15). No fructosamine values exceeded the normal reference range. Urine glucose levels were negative except trace readings in one capromorelin treated cat and one placebo treated cat. It is clear that there was no chronic hyperglycemia in capromorelin treated cats.

In conclusion, bodyweight increased significantly in the capromorelin group compared to placebo. Food consumption approached statistical significance with the capromorelin group consuming more food than the placebo group. Treatment with capromorelin caused an increase in GH, which then led to a sustained increase in IGF-1 serum levels. For some serum chemistry and hematology parameters, statistically significant changes were noted from baseline to Day 30/59/91 and overall treatment effects were found. Glucose increased over time in the capromorelin group, but no values exceeded the reference range. There was not an accompanying increase in fructosamine. The statistically significant differences for clinical pathology parameters were not clinically relevant.

Example 4—90-Day Clinical Safety & Effectiveness Study of Capromorelin in Cats

This double-masked, randomized, placebo-controlled, multisite, proof-of-concept field study tests the hypotheses that capromorelin will maintain or increase bodyweight, improve body condition score, improve muscle condition score, improve appetite and/or improve quality of life in cats. A single study protocol is followed at multiple study sites. Cats eligible for enrollment are either treated with a dosage of 2 mg/kg bodyweight of capromorelin or a placebo formulation once daily for 90±3 days.

Client-owned cats of any age, weight, breed or sex, spay/neutered with a documented decrease in bodyweight over the previous 6 months may be enrolled. Screening activities include a physical examination, rectal temperature, cardiovascular system, heart rate, respiratory system, respiratory rate, gastrointestinal system, bodyweight, peripheral lymph nodes, attitude, musculoskeletal system mucous membranes/capillary refill time, genitourinary system, eyes, state of hydration, ears, appearance of hair coat, oral cavity, skin, and neurologic system. Effectiveness variables include bodyweight, body condition, muscle condition, owner appetite assessments and owner quality of life assessments.

A body condition score (BCS) and muscle condition score (MCS) are determined by a veterinarian at Day 0, Day 14±1, Day 30±2, Day 60±3 and Day 90±3 or at the last study visit (i.e. early removal). Serum chemistry parameters are measured from blood samples taken at Day 0, Day 30±2, Day 60±3 and Day 90±3 or at the last study visit: albumin, creatine kinase (CPK), albumin/globulin ratio, globulin, alkaline phosphatase, glucose, alanine aminotransferase, blood urea nitrogen (BUN), phosphorus, calcium, potassium, chloride, sodium, cholesterol, total protein, creatinine, total bilirubin, BUN/creatinine ratio, and sodium/potassium ratio. Hematology parameters are measured at Day 0, Day 30±2, Day 60±3 and Day 90±3 or at the last study visit: white blood count (WBC), hemoglobin (HGB), red blood count (RBC), fructosamine, platelet count, platelet morphology, hematocrit (HCT), mean corpuscular volume (MCV), mean corpuscular hemoglobin (MCH), WBC differential, RBC and WBC morphology, and mean corpuscular hemoglobin concentration (MCHC). Urine samples are collected at Day 0 and Day 90±3 or at the last study visit prior to weight measurement, and tested for specific gravity, pH, color, clarity, blood, protein, bilirubin, glucose, ketones, and microscopic examination of the sediments for RBC/hpf, WBC/hpf, bacteria, epithelial cells, mucus, casts and crystals.

Each cat is assessed by the owner for quality of life and appetite at Day 0, Day 30±2, Day 60±3 and Day 90±3 or at the last study visit (i.e. early removal). For each continuous effectiveness endpoint, the changes from Day 0 to Day 14, Day 30, Day 60 and Day 90 are calculated. For bodyweight, various success criteria are defined (such as maintenance of bodyweight, 2% increase or more, 3% increase or more, etc.). Safety is evaluated based on adverse events, physical examination, IGF-1 serum levels, and serum chemistry, hematology and urinalysis parameters.

The analysis for safety evaluation is performed on a population that includes all cats that were randomized and received at least one dose of the study medication (safety population). The analysis of the effectiveness variables will be conducted on a per protocol (PP) population. The PP population will be a subset of the safety population and will comprise all cats that complete their dosing and have adequate study records. An adverse event is defined as any observation in a cat that is unfavorable and unintended and occurs after the use of capromorelin or placebo, whether or not it is considered to be product related. On Day 30±2, Day 60±3 and Day 90±3 or at the last study visit (i.e. early removal), if a laboratory result is outside the reference range and considered clinically relevant (unfavorable and unintended), these results will be reported as an adverse event.

Example 5—Two-Week Oral Toxicity Study in Cats

This study determined the safety of capromorelin when administered orally to cats. Groups of 3 male and 3 female (n=6/group) mixed breed cats were given capromorelin as an oral capsule once daily at doses of 9, 15, 30 and 60 mg/kg for 14 consecutive days. A similar group was given microcrystalline cellulose as a placebo control. All animals were observed daily for clinical signs and assessed for food consumption, with bodyweights recorded 7 days before dosing and again at euthanasia. Other measurements included periodic clinical pathology evaluations of hematology, serum chemistry and urinalysis. After the dosing period, cats were euthanized and necropsied.

Oral administration of capromorelin in cats was well tolerated. Clinical signs related to capromorelin were limited to cats in the 30 and 60 mg/kg treatment groups and consisted of emesis, sporadic salivation, and lethargy/depression. Clinical pathology changes were seen only sporadically in the 15 to 60 mg/kg dosing groups and were limited to increases in serum and urine glucose. These changes were attributed to the pharmacological actions of a GH secretagogue, and/or a stress response associated with blood drawing, not a direct toxicological effect of capromorelin. Treatment with AT-002 was not associated with any abnormal tissue findings at necropsy, both on a gross and microscopic level. The mean absolute and relative liver weights increased in females from the 30 and 60 mg/kg treatment groups and mean absolute liver weights in males at all dosages. Because of no corresponding abnormal microscopic findings, these changes in liver weights were not considered toxic.

Based on the clinical signs observed, a no-observed-adverse-effect-level (NOAEL) of 15 mg/kg/day was determined for this study. Treatment-related adverse events were limited to depression and the gastrointestinal system and only observed in the 30 mg/kg and 60 mg/kg dosing groups. Since the 30 mg/kg dose level is 15 times greater than the proposed clinically effective dose for capromorelin, it is expected that administration of capromorelin will be well tolerated in cats.

Example 6—Dose Titration Laboratory Study

This study defined a capromorelin oral solution dose regime that provides increased food intake and weight gain and the accompanying desired profile of IGF-1 serum levels. Laboratory adult cats were housed individually and divided into five groups (3/sex/group; n=6/group). Cats were dosed once daily for 10 consecutive days with either placebo, 1 mg/kg AT-002, 2 mg/kg AT-002, 3 mg/kg AT-002 or 4 mg/kg AT-002. The test article was a flavored solution formulation very similar to the final formulation. Study activities are summarized at Table 5.

The percent change in food consumption from baseline (average of Day −3, Day −2, and Day −1) compared to the treatment period (average of Day 1 through Day 10) was calculated for each cat, and is summarized at Table 6. The mean percent change from baseline to the treatment period for the placebo group increased 13.0%. The 4 mg/kg group exhibited a mean percent increase in food consumption from the baseline period to the treatment period which was statistically significant when compared to the placebo group.

TABLE 6

Food Consumption

| Group | Dose Frequency | Dose (mg/kg) | Percent Change From Baseline | P-value |
|---|---|---|---|---|
| Placebo | SID | 0 | 13.01 | |
| AT-002 | SID | 1 | 30.54 | 0.4567 |
| AT-002 | SID | 2 | 45.53 | 0.1734 |
| AT-002 | SID | 3 | 54.04 | 0.0894 |
| AT-002 (minus 5F1) | SID | 4 | 78.82 | 0.0123 |

The percent change in bodyweight from Day −1 compared to Day 10 was calculated for each cat, and is summarized at table 7. The mean percent change for the placebo group was −0.35%, indicating a decrease in weight. The 2 mg/kg AT-002 group and 3 mg/kg AT-002 group exhibited a statistically significant mean percent increase in bodyweight compared to the placebo group. The 4 mg/kg AT-002 group approached statistical significance (p=0.0502)

TABLE 7

Bodyweight

| Group | Dose Frequency | Dose (mg/kg) | Percent Change From Baseline | P-value |
|---|---|---|---|---|
| Placebo | SID | 0 | −0.35 | — |
| AT-002 | SID | 1 | 3.07 | 0.0713 |
| AT-002 | SID | 2 | 3.66 | 0.0371 |
| AT-002 | SID | 3 | 5.72 | 0.0027 |
| AT-002 (minus 5F1) | SID | 4 | 3.57 | 0.0502 |

Capromorelin was well absorbed in cats. Maximum serum concentrations generally occurred within 30 min post-dose. As expected, the 4 mg/kg capromorelin treatment had a serum profile with the highest levels. In general, concentrations of capromorelin in all AT-002 treated groups had declined to very low levels by 8 hours post-dose. In addition, measurable concentrations of capromorelin were not detected or very low in the 0 hour samples on Day 10 of

TABLE 5

Study Activities.

Figure 16:
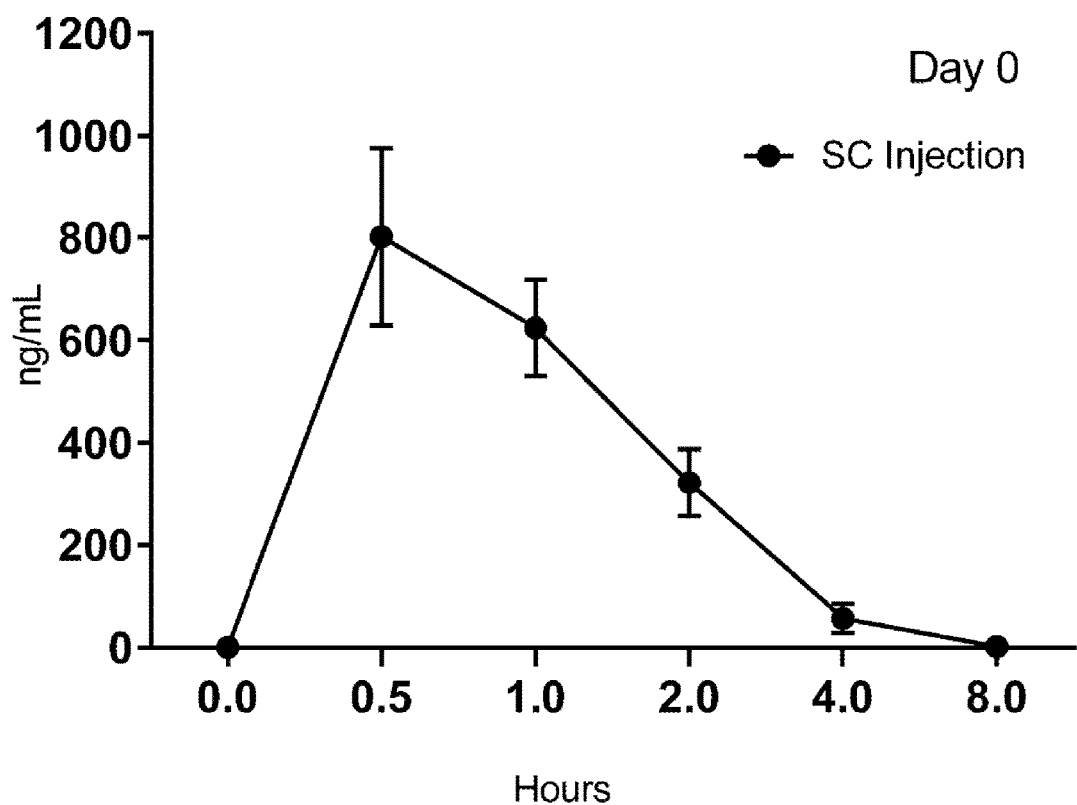
FIG. 16 shows the mean capromorelin serum levels at Day 1 in a dose titration study in cats.
Figure 17:
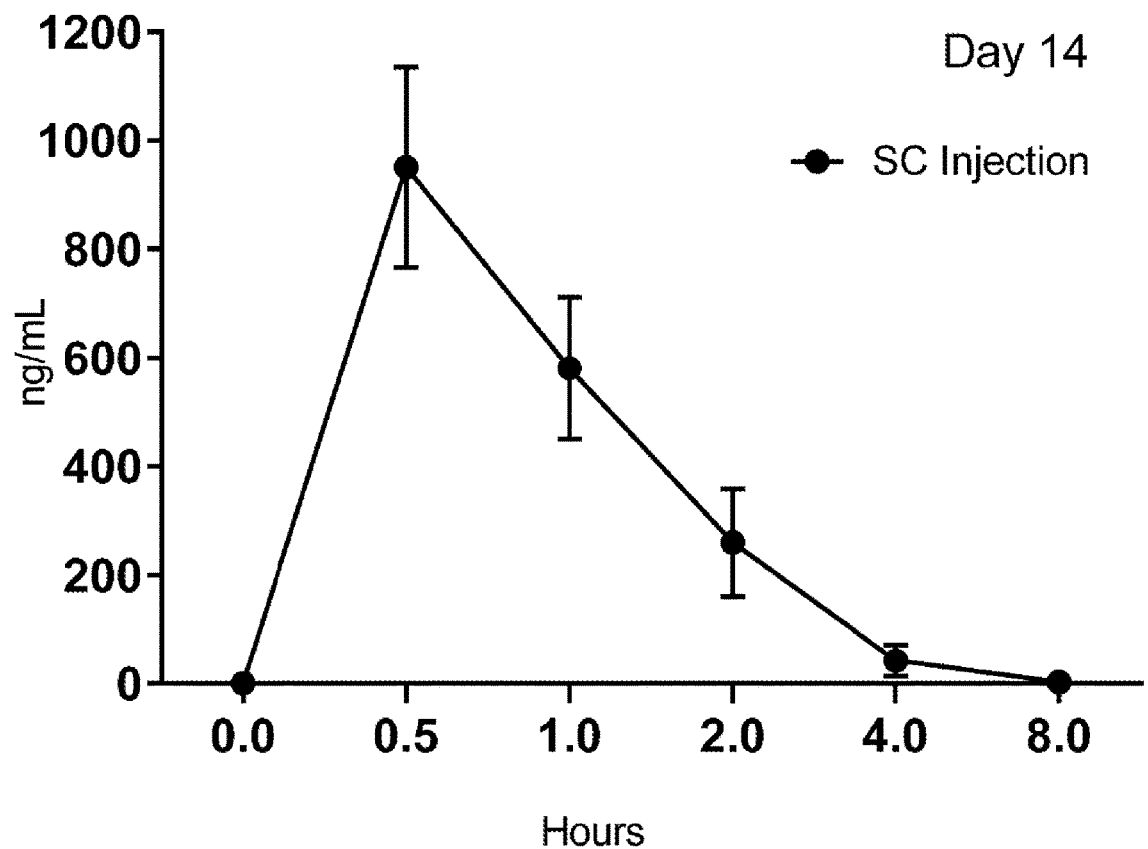
FIG. 17 shows the mean capromorelin serum levels at Day 13 in a dose titration study in cats.

| Parameter | −7 to −2 | −1 | 1 | 2 | 3 | 4 | 5 | 6 | 7 | 8 | 9 | 10 |
|---|---|---|---|---|---|---|---|---|---|---|---|---|
| Physical Exam | X | | | | | | | | | | | |
| Dosing | | | X | X | X | X | X | X | X | X | X | X |
| Food Consumption | X | X | X | X | X | X | X | X | X | X | X | X |
| Body Weight | X | X | | | | | X | | | | | X |
| Serum Analysis: Capromorelin | | | X | | | | | | | | | X |
| Serum Analysis: IGF-1 | | | X | | | | | | | | | X | cats treated with AT-002. There was no evidence of capromorelin accumulation in serum (FIGS. 16 and 17).

Figure 18:
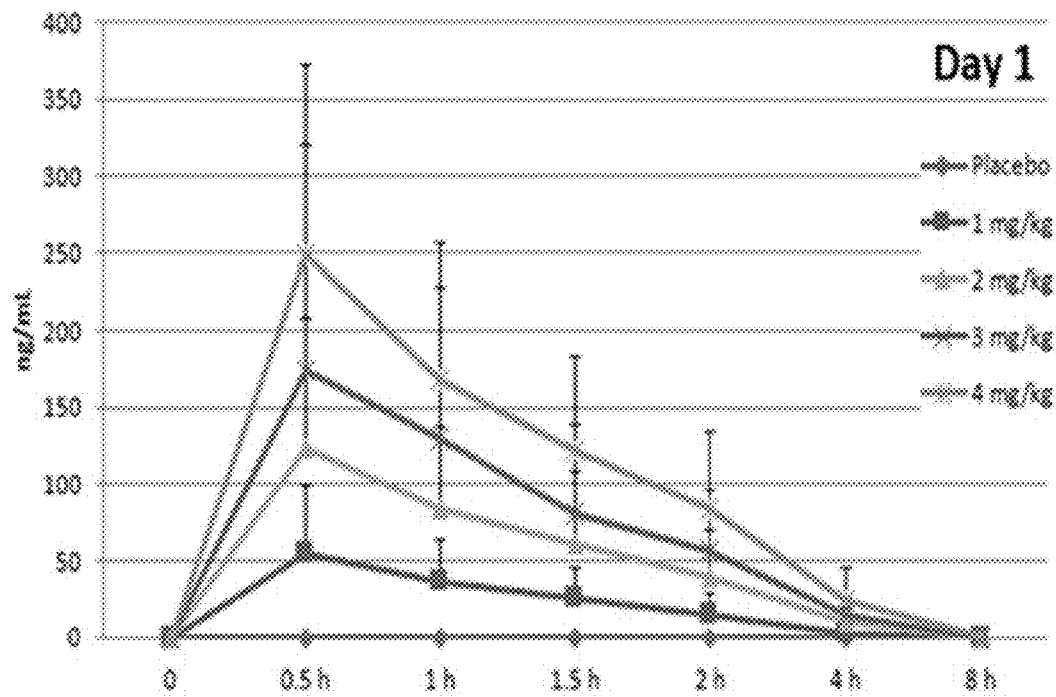
FIG. 18 shows the mean capromorelin serum levels from a dose titration study in cats at Day 1.
Figure 19:
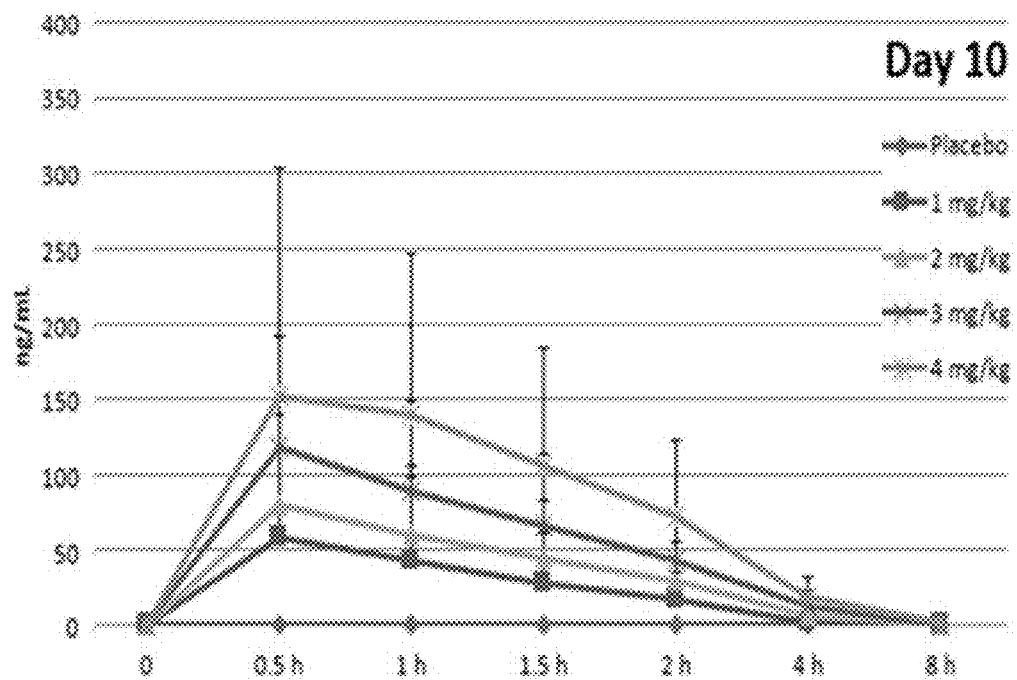
FIG. 19 shows the mean capromorelin serum levels from a dose titration study in cats at Day 10.

Changes in serum IGF-1 levels attributable to the test article were observed in males and females following dosing on Days 1 and 10. The IGF-1 serum profile in the placebo group remained steady at baseline on Days 1 and 10. The initial IGF-1 response (increase) occurred at about 4 hours following treatment with AT-002 and achieved its maximum relatively steady level by 8 hours post-dose on Days 1 and 10. IGF-1 levels were elevated, compared to the controls, in a sustained manner over the previous 24 hour period on Day 10. The magnitude of the IGF-1 sustained elevation was greatest following 3 mg/kg dosing compared with the other dose groups (FIGS. 18 and 19).

Treatment of AT-002 for 10 days increased mean food consumption and bodyweight compared to the placebo group. The 2 mg/kg AT-002 group and 3 mg/kg AT-002 group exhibited the best increase weight gain. Capromorelin was well-absorbed from the flavored solution formulation and resulted in drug serum levels adequate to stimulate an apparent increase in serum GH, as evinced by the desired sustained serum IGF-1 levels. IGF-1 levels exhibited a sustained increase over a 24 hour period in treated animals by Day 10 in all AT-002 treatment groups.

Overall, once-a-day dosing of AT-002 was sufficient to result in 24 hours of elevated IGF-1 levels post-dose, the desired profile for suppressing the over-stimulation of GH and cortisol.

Example 7. Cat Dose Titration Laboratory Study

This study tested the effectiveness of an oral formulation of AT-002 in laboratory cats and to select a dose that would cause increased food intake and weight gain. This study investigated the effects of a capromorelin oral solution in cats dosed at 1 mg/kg, 2 mg/kg or 3 mg/kg compared to placebo (n=8/group) for 21 days. Food consumption was measured each day from Day −10 through Day 21. For each cat, baseline food consumption was calculated as the average of Days −3, −2 and −1. The percent change from baseline to treatment period was calculated as 100× (treatment period minus baseline)/baseline. Bodyweight was measured on Day 1, Day 8, Day 15 and Day 22. Baseline bodyweight was defined as the value collected on Day 1 (prior to treatment).

The mean percent change from baseline (Day −3 to Day −1) to treatment period (Day 1 to Day 21) in food consumption for each treatment group is found at Table 8. The placebo group showed an increase of 10.8%. Groups 2, 3 and 4 increased 25.3%, 45.7% and 29.6% respectively (p=0.0066 for all treatment groups compared to the placebo group).

TABLE 8

Food Consumption

| Group | Dose (mg/kg) | Mean % Change (±SD) in Consumption Over 21 Days | P value |
|---|---|---|---|
| Placebo | 0 | 10.83 ± 10.48 | — |
| AT-002 | 1 | 25.32 ± 16.70 | 0.1203 |
| AT-002 | 2 | 45.67 ± 24.39 | 0.0007 |
| AT-002 | 3 | 29.59 ± 13.65 | 0.0545 |

The mean percent change from baseline (Day 1) to Day 22 in bodyweight for each treatment group is presented in the table below. There were statistically significant increases in bodyweight when comparing each of the three AT-002 treated groups to the placebo group (p=0.0103 for all treatment groups compared to the placebo group).

TABLE 9

Bodyweight

| Group | Dose (mg/kg) | Mean % Change (±SD) in Bodyweight Over 21 Days | P value |
|---|---|---|---|
| Placebo | 0 | −1.11 ± 1.84 | — |
| AT-002 | 1 | 5.41 ± 4.11 | 0.0067 |
| AT-002 | 2 | 6.61 ± 5.05 | 0.0018 |
| AT-002 | 3 | 3.92 ± 5.15 | 0.0372 |

While treatment with 1 mg/kg showed an increase in mean food consumption, it was not statistically significant when compared to placebo. Therefore, the 2 mg/kg treatment group which showed a statistically significant increase in food consumption and bodyweight compared to placebo treated cats was chosen as the proposed clinical dose in cats.

The studies from Example 6 and the present Example 7 characterize a once daily dose effective between 2 mg/kg and 3 mg/kg in healthy laboratory cats. Given that capromorelin has a wide safety margin in cats in three pilot studies, a chronic dose regime of 2 mg/kg SID was chosen. These two studies were conducted according to the principles of GLP. The test facility strictly performed the appropriate procedures per the protocol and their applicable standard operating procedures. However, there was no QA component, so these studies are non-GLP.

Example 8—Laboratory Cats Modelling CKD Safety Pilot Study

This study sought to define a capromorelin pharmacokinetic profile in serum of cats with compromised kidney function, to determine if accumulation of capromorelin in serum occurred after 14 days of treatment, and to observe cats for any potential adverse effects of treatment not seen in normal cats. The target population for the capromorelin oral solution included cats with CKD. Therefore, this study used laboratory with significant portions of their kidneys surgically removed and subsequently compromised kidney function indicated by increased serum creatinine and BUN. These cats were developed as a model by Charles River, and are maintained at a colony at their facility in Ballina, Ireland.

Sixteen cats with compromised kidney function were enrolled in the study and randomized to three groups. Animals assigned to Group 1 (n=6) were administered AT-002 once on Day 0 by intravenous catheter at a dose rate of 0.75 mg/kg per cat. Animals assigned to Group 2 (n=6) were administered the AT-002 daily for 14 days by subcutaneous injection at a dose rate of 2 mg/kg. Subcutaneous and intravenous treatment routes were used to assure that sufficient drug exposure occurred. Animals assigned to Group 3 (n=4) served as untreated controls.

Blood samples were collected for capromorelin and/or IGF-1 analysis from animals assigned to Group 1 on Study Day 0. Blood samples were also collected from animals assigned to Groups 2 and 3 on Study Days −1 and 13 (prior to dosing) for hematology and clinical chemistry analysis. Appetite was assessed by food intake and weight gain. Bodyweight measurements were performed on Days −7, −1 (all groups) and on Day 13 (Groups 2 and 3 only). Food intake was monitored from Day −7 to Day 13 inclusive for animals assigned to Groups 2 and 3. Animals were observed daily for clinical signs.

Figure 20:
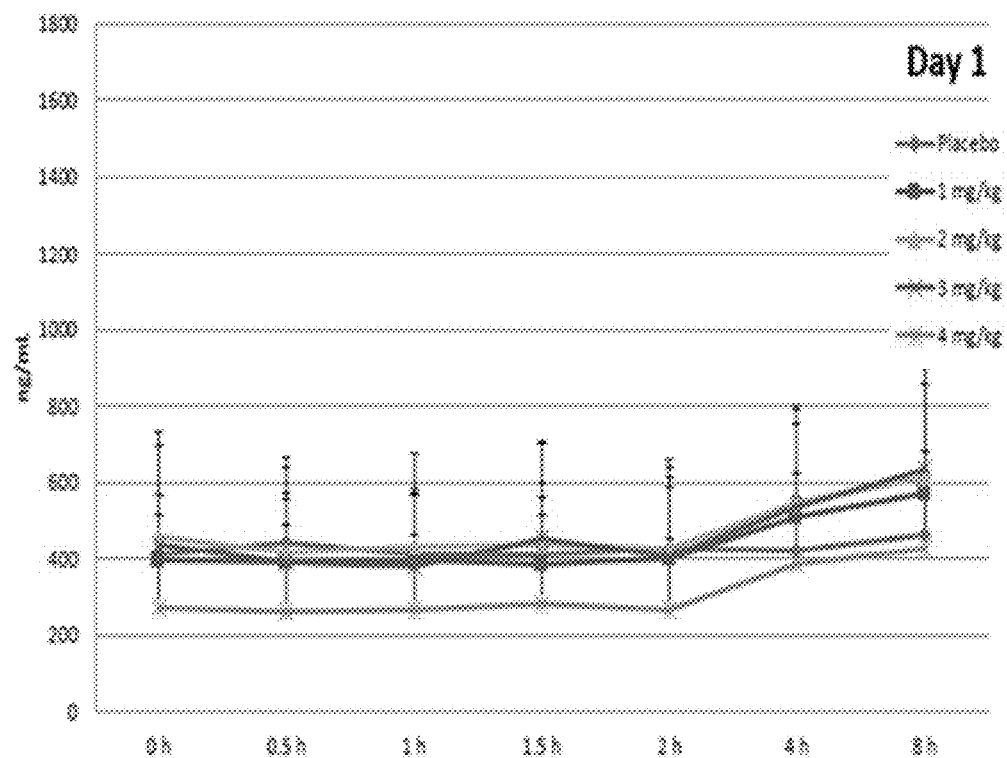
FIG. 20 shows the mean capromorelin serum levels in laboratory cats modeling CKD at Day 0 of a safety pilot study.
Figure 21:
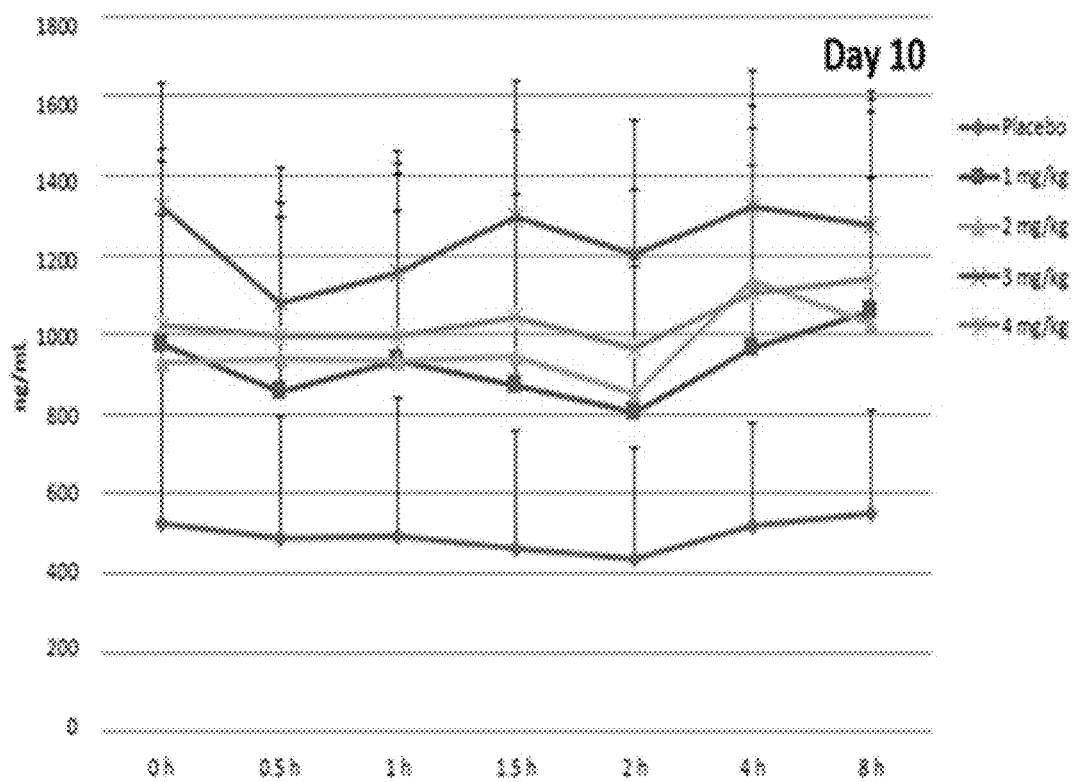
FIG. 21 shows the mean capromorelin serum levels in laboratory cats modeling CKD at Day 13 of a safety pilot study.
Figure 22:
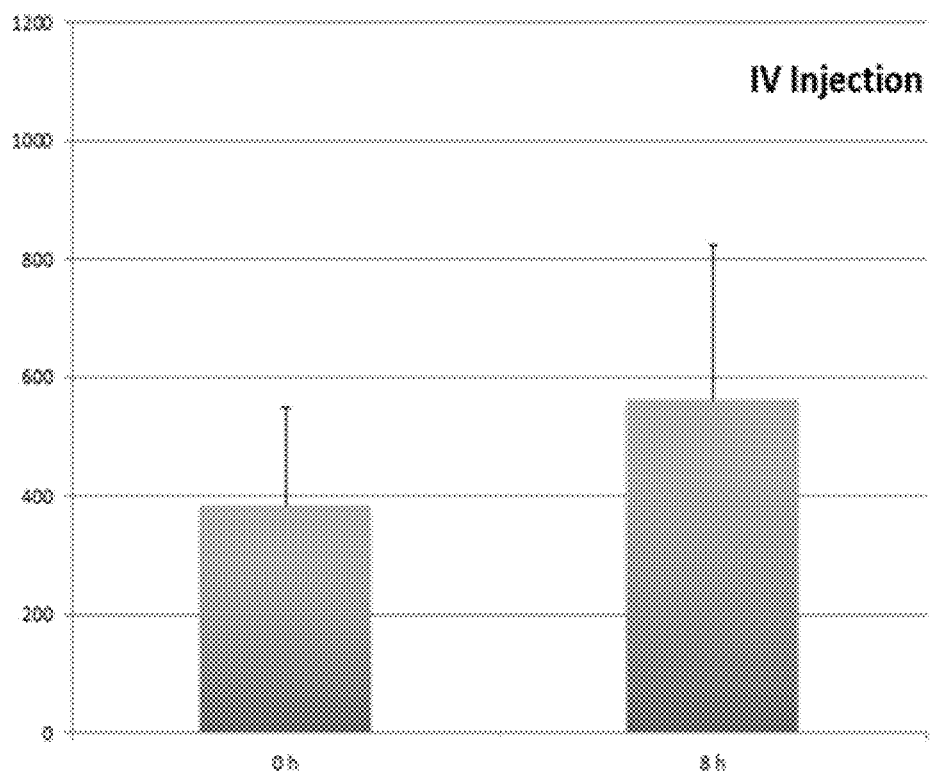
FIG. 22 shows the mean IGF-1 serum levels (ng/mL) in laboratory cats modeling CKD at Day 0 of a safety pilot study.
Figure 23:
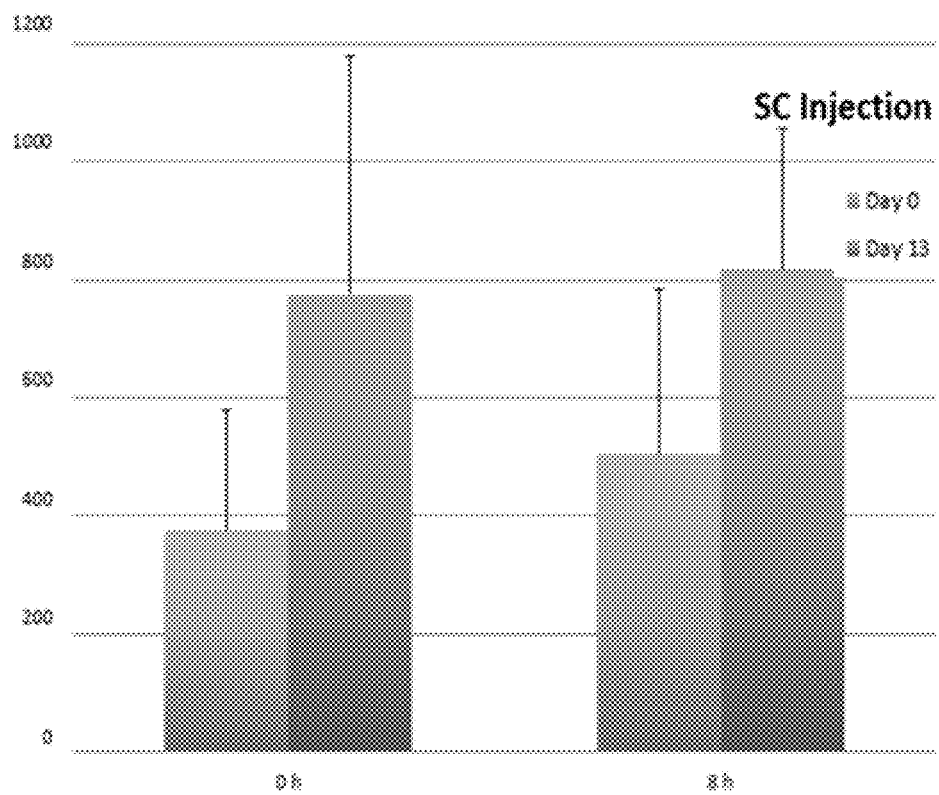
FIG. 23 shows the mean IGF-1 serum levels (ng/mL) in laboratory cats modeling CKD at Day 13 of a safety pilot study.

The pharmacokinetic profiles of cats following capromorelin treatment (IV or SC) showed drug exposure and no evidence of drug accumulation (FIGS. 20 and 21). Capromorelin increased IGF-1 levels in cats treated with 2 mg/kg AT-002 on Day 0 (FIG. 22). This increase in IGF-1 became sustained by Day 13. On Day −1 and Day 13, hematology and clinical chemistry were monitored in cats in Group 2 (SC) and Group 3 (control) to assess if there was any effect of capromorelin treatment (FIG. 23).

In all cases where results for a hematology or clinical chemistry parameter were outside the reference range, there were no clinical signs of illness associated with any incidence. Parameters outside the reference ranges were similar on Day −1 and Day 13 with only minor variation in results. No incidence is treatment related. In all cases the results were only slightly higher or slightly lower than the reference range.

From Day −7 to Day 13, all animals assigned to Group 2 (AT-002 at 2 mg/kg/day; subcutaneous) and Group 3 (untreated control) lost bodyweight. All animals assigned to all treatment groups did not consume all their food. This is most likely due to food being removed about 4 hours after it was offered. Absent statistical analysis, even with a small numerical difference, the mean food intake between animals assigned to Group 2 (AT-002) and animals assigned to Group 3 (untreated control) at each time point did not differ.

AT-002, when administered subcutaneously to cats with a compromised kidney function, was unable to stimulate appetite as there was no apparent increase in food intake or bodyweight. It may be that the oral route of absorption is required for AT-002 to stimulate appetite, as ghrelin is a hormone produced by the stomach. Capromorelin resulted in a sustained increase in IGF-1 levels in cats treated with 2 mg/kg AT-002 by subcutaneous injection for 14 days.

Example 9—Safety and Effectiveness of Daily Capromorelin in Cats with CDK for 90 Days at an Oral Dose of 2 mg/kg This study was to confirm the safety and effectiveness of AT-002 (capromorelin) in cats under field conditions using a dose of 2 mg/kg administered once daily for 90 days. The study tested the hypotheses that AT-002 will maintain or increase bodyweight, improve body condition score (BCS), improve muscle condition score (MCS), improve appetite and/or improve quality of life (QoL) in cats. This was a double-masked, randomized, placebo-controlled, multi-site, proof of concept field study.

This study enrolled cats diagnosed with chronic kidney disease (CKD) and a minimum 6-month history of losing weight. The enrollment target was for a minimum of 15 evaluable cases in the AT-002 group and 15 evaluable cases in the Control Product (CP; placebo) group. The Investigator and all study personnel were masked to treatment code (A or B) and treatment group (AT-002 or CP). The Dispenser and Owner remained blinded to treatment group (AT-002 or CP).

Cats were treated with a dosage of 2 mg/kg body weight of AT-002 (AT-002) or a placebo (CP) formulation at the same dose volume as the AT-002 once daily for 90±3 days. Day 0 was the first day of dosing. Cats were evaluated on Day 0, Day 14±1, Day 30±2, Day 60±3 and Day 90±3. The primary effectiveness variable was change in bodyweight from Day 0 through Day 90±3. Secondary effectiveness variables included BCS, MCS, owner appetite assessments and owner QoL assessments.

After enrollment, each case was randomly assigned to AT-002 or CP in a 1:1 ratio. The enrollment target was at least 30 evaluable cases (15 AT-002 and 15 CP) per the study randomization schedule across all sites.

Cats included in the study were spayed/neutered cats of any age and breed with a documented historical decrease in bodyweight over the previous 6 months, and a diagnosis of chronic kidney disease (IRIS stages II, III or IV). Cats on medications for certain stable, chronic conditions were allowed. Excluded from the study were cats in crisis or moribund, cats with documented and uncontrolled hyperthyroidism or inflammatory bowel disease, cats in which food intake is contraindicated (i.e. suspected foreign body, gastrointestinal surgery), cats with dental disease severe enough to impair food intake, cats with diabetes, and cats currently receiving prohibited medications.

The Owner maintained the feeding regime the cat was on at study enrollment. No special foods and no special feeding schedule were required. Water was available ad libitum. The cat's diet was monitored and a "Diet History" completed when the Investigator interviewed the Owner at screening/qualification (Day 0), Day 30±2, Day 60±3 and Day 90±3 or at the last study visit (i.e. early removal).

During the study, a cat was treated with medications that the cat was taking to control ongoing, pre-existing medical condition that was well stabilized. Antiemetics (e.g. maropitant citrate (Cerenia™)) were allowed during the study if prescribed before the study started and the treatment was stable (i.e. cat was on treatment regimen with no changes for a minimum of 2 days prior to Day 0). A total of 6 cats received one or more doses of Cerenia before, during or after the study.

No parenteral fluids were allowed to be given within approximately 12 hours prior to the Day 14±1, Day 30±2, Day 60±3 and Day 90±3 visit. Systemic corticosteroids were prohibited within the last 30 days with the exception of cats stabilized on long-term treatment. Anabolic steroids, progesterone, and Epogen/darbepoetin were prohibited within 30 days of Day 0. Mirtazapine, dronabinol, cyproheptadine and diazepam were prohibited within 7 days of Day 0.

Bodyweight was measured in pounds to the nearest tenth decimal place as part of the physical examination at screening/qualification/Day 0, Day 14±1, Day 30±2, Day 60±3 and Day 90±3 and at the time of any unscheduled visit or early removal from the study.

A body condition score (BCS) was determined by the Investigator/Examining Veterinarian as part of the physical examination at screening/qualification (Day 0), Day 14±1, Day 30±2, Day 60±3 and Day 90±3 or at the last study visit (i.e. early removal) using the following 9-point scale:

1—Emaciated—Ribs visible on shorthaired cats; no palpable fat; severe abdominal tuck; lumbar vertebrae and wings of ilia easily palpated.

2—Very Thin—Ribs easily visible on shorthaired cats; lumbar vertebrae obvious with minimal muscle mass; pronounced abdominal tuck; no palpable fat.

3—Thin—Ribs easily palpable with minimal fat covering; lumbar vertebrae obvious; obvious waist behind ribs; minimal abdominal fat.

4—Underweight—Ribs palpable with minimal fat covering; noticeable waist behind ribs; slight abdominal tuck; abdominal fat pad absent.

5—Ideal—Well-proportioned; observe waist behind ribs; ribs palpable with slight fat covering; abdominal fat pad minimal.

6—Overweight—Ribs palpable with slight excess fat covering; waist and abdominal fat pad distinguishable but not obvious; abdominal tuck absent.

7—Heavy—Ribs not easily palpated with moderate fat covering; waist poorly discernible; obvious rounding of abdomen; moderate abdominal fat pad.

8—Obese—Ribs not palpable with excess fat covering; waist absent; obvious rounding of abdomen with prominent abdominal fat pad; fat deposits present over lumbar area.

9—Grossly Obese—Ribs not palpable under heavy fat cover; heavy fat deposits over lumbar area, face and limbs; distention of abdomen with no waist; extensive abdominal fat deposits.

A MCS was determined by the Investigator/Examining Veterinarian as part of the physical examination at screening/qualification (Day 0), Day 14±1, Day 30±2, Day 60±3 and Day 90±3 or at the last study visit (i.e. early removal) using the following 4-point scale:

3—Normal muscle mass on palpation over the spine, scapulae, skull, or wings of the ilia 2—Mild muscle loss on palpation over the spine, scapulae, skull, or wings of the ilia 1—Moderate muscle loss on palpation over the spine, scapulae, skull, or wings of the ilia 0—Severe muscle loss on palpation over the spine, scapulae, skull, or wings of the ilia Blood samples for serum chemistry were collected at the screening/qualification/Day 0, Day 30±2, Day 60±3 and Day 90±3 visits or at the last study visit (i.e. early removal). The blood samples were analyzed for albumin, glucose, alkaline phosphatase (ALP), phosphorus, alanine aminotransferase (ALT), potassium, blood urea nitrogen (BUN), sodium, calcium, total bilirubin, chloride, total protein, cholesterol, albumin/globulin ratio, creatinine kinase (CPK), BUN/creatinine ratio, creatinine, sodium/potassium ratio, globulins, white blood cell count (WBC), platelet count, red blood cell count (RBC), platelet morphology, hemoglobin (HGB), WBC differential, hematocrit (HCT), RBC and WBC morphology, mean corpuscular volume (MCV), fructosamine, mean corpuscular hemoglobin (MCH), and mean corpuscular hemoglobin concentration (MCHC).

Urine samples were collected at the screening/qualification/Day 0, Day 30±2, Day 60±3 and Day 90±3 visits or at the last study visit (i.e. early removal). The urine samples were analyzed for color, glucose, clarity, ketones, specific gravity, bilirubin, pH, blood, protein, and sediment (microscopic evaluation).

A 1-mL blood sample was collected into a vacutainer tube containing no anticoagulant at the screening/qualification/Day 0, Day 30±2, Day 60±3 and Day 90±3 or at the last study visit (i.e. early removal). Blood samples were kept at room temperature and allowed to clot for about 1 hour. Clotted samples were centrifuged for approximately 15 minutes at 3000 RPM.

Each cat was assessed for appetite by the Owner the screening/qualification/Day 0, Day 30±2, Day 60±3 and Day 90±3 or at the last study visit (i.e. early removal). Each cat was also assessed for QoL by the Owner at the veterinary clinic at screening/qualification/Day 0, Day 30±2, Day 60±3 and Day 90±3 or at the last study visit (i.e. early removal).

The cat was the experimental unit. All tests of statistical significance were completed at a two-sided alpha level of 0.05. The level of significance for the safety variables was alpha=0.10, two-sided. Assumptions of normality of residuals were investigated for each continuous response measurement. If the normality assumption was rejected at the 1% level with the Shapiro-Wilk test, then values were ranked in ascending order with tied values given a mean rank before running statistical models. Missing data was not imputed and only observed data were included in the statistical models.

For bodyweight, the primary effectiveness variable compared mean percent changes for the AT-002 and CP groups. For the AT-002 group, statistically significant changes from Day 0 were found for Day 14 (p=0.0013), Day 30 (p=0.0007), Day 60 (p=0.0144) and Day 90 (p=0.0434). No statistically significant changes from Day 0 were found for the CP group. This establishes that cats treated with AT-002 gained weight during the treatment period, while the CP group did not gain weight. When comparing the mean percent weight changes between the AT-002 group and the CP group, the AT-002 group was statistically significantly higher at Day 30 (p=0.0248), Day 60 (p=0.0018) and Day 90 (p=0.0093).

For bodyweight, a secondary effectiveness variable defined success for an individual cat based on several weight gain scenarios. For the success criteria of "Maintenance or Gain", the percent change from Day 0 to Days 14, 30, 60 and 90 was not statistically significantly different between groups. For the success criteria of "Greater than 0% Gain", the percent changes from Day 0 to Day 14 (p=0.0259), to Day 30 (p=0.0083), and to Day 90 (p=0.0178) were found to be statistically significantly different and favored the AT-002 group. For the success criteria of "Greater than 1% Gain", the percent changes from Day 0 to Day 30 (p=0.0178) and to Day 90 (p=0.0178) were found to be statistically significantly different and favored the AT-002 group. For the success criteria of "Greater than 2% Gain", the percent change from Day 0 to Day 14 (p=0.0401) was found to be statistically significantly different and favored the AT-002 group.

For the body condition score, muscle condition score, owner appetite assessment and quality of life parameters, no meaningful statistical differences were observed. Of the three quality of life parameters measured, the mean descriptive (monthly) quality of life parameter showed an increase (improvement) in the placebo group from Day 0 to Day 90, but the AT-002-treated group mean score remained the same. This difference was significant (p=0.0038).

This study demonstrated that AT-002 was well-tolerated in cats. Given the pre-existing renal disease, loss of bodyweight over at least the previous 6 months, and other concomitant conditions present in these cats, adverse events were expected. Renal disease and its progressive nature may account for many observations in AT-002 treated cats, including clinical pathology changes, inappetance, dehydration, weight loss, etc.

AEs were reported more often in AT-002 treated cats than placebo treated cats, but none were unexpected and only 1 of 5 SAEs was deemed related to AT-002/CP treatment. The veterinarian indicated a "probable" relationship to AT-002/CP treatment for an SAE for anorexia, which was associated with a gastrointestinal event. It is unclear whether AT-002 caused this event or if some other factor did. Many AEs were associated with pre-existing conditions or events unrelated to the study. AEs reported in greater than 10% of the overall population were inappetance, vomiting, increased salivation and diarrhea/loose stool, although there was evidence for a potential relationship to the AT-002 treatment only for increased salivation and potentially vomiting. Some parameters of the physical examination findings were different between groups, but none was both clinically significant and related to AT-002 treatment. Changes in clinical pathology data from Day 0 to the end of study visit were noted more often in the AT-002 group. However, no clinical pathology changes were considered likely to be clinically significant.

An increase in IGF-1 serum levels following AT-002 administration confirmed the physiology of the GH/IGF-1 axis worked as expected.

Thus, the results of this study confirm that chronic administration of AT-002 at a dose of 2 mg/kg once daily is well-tolerated and manages weight maintenance/gain in cats with CKD that are losing weight. The key primary and secondary effectiveness variables showed a statistically significant superiority of AT-002 compared to placebo.

Example 11—Pilot Clinical Field Study

This placebo controlled, masked non-GCP study was to confirm the safety and effectiveness (weight gain) of AT-002 (capromorelin) at a dose of 2 mg/kg administered once daily for 90 days in cats with CKD and a history of losing weight.

A total of 42 cats were screened at 7 veterinary clinics. Of these 42 cats, 1 was a screen failure, resulting in 41 cats being enrolled and randomized to 1 of 2 treatments, capromorelin oral solution (AT-002) or placebo (CP). Eligible study candidates included cats that presented to the veterinary clinic with a diagnosis of CKD (IRIS stages II, III or IV) and a documented decrease in bodyweight over the previous 6 months. Test articles were provided as flavored oral solutions and were administered orally once daily beginning on Day 0 for 90±3 days, AT-002 at a dose rate of 2 mg/kg and CP at the equivalent dose volume to AT-002. The Investigator, study staff and cat Owners were masked to treatment. Cats were re-evaluated at the clinic on Day 14±1, Day 30±2, Day 60±3 and Day 90±3.

The key variable for the determination of effectiveness was bodyweight. Other effectiveness variables measured included body condition score, muscle condition score, quality of life assessments (unvalidated) and owner appetite assessments (unvalidated). Safety was assessed by physical examinations, clinical pathology testing (hematology and serum chemistry), urinalysis, serum IGF-1 levels and adverse event monitoring.

Mean bodyweights for the capromorelin treatment group increased during the 90-day treatment period when compared to the placebo group (p=0.0067) (analysis used PPP1; Table 10). By Day 30, mean bodyweight (±SEM) was increased 3.86%±0.85% in the capromorelin group compared to 0.20%±0.75% in the placebo group (P=0.0248). On Day 60, mean bodyweight (±SEM) was increased 4.06%±1.42% in the capromorelin group compared to −1.14%±1.20% in the placebo group (p=0.0018). On Day 90, mean bodyweight (±SEM) increased 3.59%±1.59% in the capromorelin group compared to −0.69%±1.23% in the placebo group (p=0.0093).

TABLE 10

Pilot Clinical Field Study - Bodyweight - Treatment Means Comparison

| | Capromorelin (n = 13) | Placebo (n = 17) | P value |
|---|---|---|---|
| Day 14 | 2.93% ± 0.70% | 0.57% ± 0.57% | 0.1406 |
| Day 30 | 3.86% ± 0.85% | 0.20% ± 0.75% | 0.0248 |
| Day 60 | 4.06% ± 1.42% | −1.14% ± 1.20% | 0.0018 |
| Day 90 | 3.59% ± 1.59% | −0.69% ± 1.23% | 0.0093 |

If individual patient success is defined as "maintenance or gain" and successes are counted per treatment group, the capromorelin group included more "successes"; however, the groups did not differ significantly on any day (analysis used PPP2; Table 11). If individual patient success is defined as "greater than 0% gain" and successes counted per treatment group, the capromorelin treatment group had significantly more successes compared to the placebo group on Day 14 (p=0.0259), Day 30 (p=0.0083) and Day 90 (p=0.0178) (analysis used PPP2; Table 12).

TABLE 11

Pilot Clinical Field Study - Bodyweight - Success Defined as Maintenance or Gain

| | Capromorelin (n = 15) | Placebo (n = 18) | P value |
|---|---|---|---|
| Day 14 | 13/15 (86.7% Success) | 13/18 (72.2% Success) | 0.3291 |
| Day 30 | 14/15 (93.3% Success) | 11/18 (61.1% Success) | 0.0648 |
| Day 60 | 12/15 (80.0% Success) | 8/18 (44.4% Success) | 0.0533 |
| Day 90 | 12/15 (80.0% Success) | 8/18 (44.4% Success) | 0.0533 |

TABLE 12

Pilot Clinical Field Study - Body Weight - Success Defined as Greater Than 0% Gain

| | Capromorelin (n = 15) | Placebo (n = 18) | P value |
|---|---|---|---|
| Day 14 | 13/15 (86.7% Success) | 8/18 (44.4% Success) | 0.0259 |
| Day 30 | 13/15 (86.7% Success) | 6/18 (33.3% Success) | 0.0083 |
| Day 60 | 10/15 (66.7% Success) | 6/18 (33.3% Success) | 0.0711 |
| Day 90 | 11/15 (73.3% Success) | 5/18 (27.8% Success) | 0.0178 |

Mean body condition score (on a scale of 1 to 9; see Example 9) in the capromorelin treated cats increased slightly. While the mean score in the placebo treated group decreased slightly, these differences were not statistically significant (p=0.4650) (analysis used PPP1).

Mean muscle condition score (on a scale of 0 to 3; see Example 9) was increased in both treatment groups, but the increase was slightly greater in capromorelin treated group compared to placebo. However, this difference was not statistically significant (p=0.4095) (analysis used PPP1).

Mean descriptive quality of life monthly scores (on a scale of 1 to 5) for the placebo group increased during the 90-day treatment period when compared to the capromorelin treatment group (p=0.0404) (analysis used PPP1). On Day 0 (baseline), the mean descriptive quality of life monthly score (±SEM) was 3.85±0.19 in the capromorelin group compared to 3.35±0.17 in the placebo group (p=0.0588). On Day 90, the change in the mean descriptive quality of life monthly score (±SEM) from Day 0 was increased 0.76±0.16 in the placebo group compared to 0.00±0.11 in the capromorelin group (P=0.0038). By this monthly measure the placebo group quality of life improved during the study, while the capromorelin group quality of life stayed the same.

Mean descriptive owner appetite assessment monthly scores did not change significantly for the capromorelin group compared to the placebo group on Day 30 (p=0.7300), Day 60 (p=0.1446) or Day 90 (p=0.8518) (analysis used PPP1).

Mean IGF-1 levels at baseline in the capromorelin group were lower than the placebo group cats, but because of variability this difference was not statistically significant. Mean IGF-1 serum levels for the capromorelin group increased over baseline when compared to the placebo group during the 90-day treatment period (p=0.0202) (analysis used PPP1; Table 13). On Day 30, mean (±SEM) IGF-1 serum levels were increased over baseline (Day 0) by 274.60 ng/mL±49.06 ng/mL in the capromorelin group compared to 28.62 ng/mL±43.46 ng/mL in the placebo group (p=0.0030).

TABLE 13

Pilot Clinical Field Study - IGF-1 Serum Levels

| | Capromorelin | | Placebo | |
|---|---|---|---|---|
| | Mean Levels (SEM) | Change | Mean Levels (SEM) | Change |
| Day 0 | 556.91 ± 64.30 | | 764.31 ± 89.41 | |
| Day 30 | 855.60 ± 72.74 | 274.60 ± 49.06 | 792.92 ± 69.41 | 28.62 ± 43.46 |
| Day 60 | 752.55 ± 56.89 | 195.64 ± 40.70 | 833.67 ± 90.83 | 41.83 ± 51.27 |
| Day 90 | 720.73 ± 65.70 | 163.82 ± 52.74 | 790.31 ± 80.38 | 26.00 ± 43.62 |

Safety observations included monitoring adverse events and measuring clinical pathology parameters (serum chemistry, hematology and urinalysis). This study demonstrated that capromorelin was well-tolerated in cats. Given the pre-existing renal disease and loss of bodyweight over at least the previous 6 months and other concomitant conditions present in these cats, adverse events were expected. Renal disease and its progressive nature may account for many observations in capromorelin treated cats, including clinical pathology changes, inappetance, dehydration, weight loss, etc. AEs were reported more often in capromorelin-treated cats than in placebo-treated cats, but none was unexpected and only 1 of 5 SAEs was deemed related to AT-002/CP treatment. The veterinarian indicated a "probable" relationship to AT-002/CP treatment for an SAE for anorexia, which was associated with a gastrointestinal event. It is unclear if capromorelin caused this event or if some other factor did. Many AEs were associated with pre-existing conditions or events unrelated to the study. AEs reported in greater than 10% of the overall population were inappetance, vomiting, increased salivation and diarrhea/loose stool, although there was evidence for a potential relationship to capromorelin treatment only for increased salivation and potentially vomiting. Some parameters of the physical examination findings were different between groups, but none was both clinically significant and related to AT-002 treatment. Changes in clinical pathology data from Day 0 to the end of study visit were more frequent in the AT-002 group. However, no clinical pathology changes were considered likely to be clinically significant. Increased IGF-1 serum levels following AT-002 administration confirmed the expected physiology of the GH/IGF-1 axis.

If individual patient success is defined as "maintenance or gain", groups did not differ significantly on any day. However, the capromorelin group had significantly more "successes" compared to the placebo group and this difference approached significance on Day 30, Day 60 and Day 90. If individual patient success as defined as "greater than 0% gain", the capromorelin group had significantly more "successes" compared to the placebo group on Day 14 (p=0.0259), Day 30 (p=0.0083), and Day 90 (p=0.0178).

Body condition score and muscle condition score showed an increasing trend for the capromorelin-treated group compared to the placebo group from Day 0 to Day 90. These trends were not statistically significant.

IGF-1 serum levels increased statistically significantly over baseline during treatment in the capromorelin group compared to the placebo group. At Day 30, the increase in IGF-1 serum levels for the capromorelin group versus the placebo group was statistically significant, but within a normal physiological range. At Days 60 and 90, the trends of increased IGF-1 serum levels over baseline continued for the capromorelin group compared to the placebo group; however, these trends were not statistically different. As expected, the increases in IGF-1 serum levels represented a modest increase back to levels that would be expected in a younger cat.

Thus, chronic administration of capromorelin oral solution at a dose of 2 mg/kg once daily is well-tolerated and managed weight maintenance/gain in cats with CKD that were losing weight. The increased bodyweight for the capromorelin group versus the placebo group was statistically significant at Day 30 and remained significant on Days 60 and Day 90. When comparing treatments, the increased bodyweight for the capromorelin group versus the placebo group was statistically significant at Day 30 and remained significant on Days 60 and Day 90. The placebo group lost weight from Day 0 to Day 90. The safety profile associated with capromorelin was similar to that of placebo. Measurement of weight was the clinical pivotal parameter. Weight gain assures an improving overall state for the cat and provides a clear clinical benefit.

All compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A method of binding growth hormone secretagogue receptors (GHS-Rs) with capromorelin in the hypothalamus of a companion animal or livestock,
   the method comprising administering a therapeutically effective amount of a capromorelin-containing composition to a companion animal or livestock in need thereof at least once per day for a period of at least 30 days;
   wherein the capromorelin-containing composition comprises from about 0.5 milligrams to about 7.5 milligrams of capromorelin per kilogram of bodyweight of the companion animal or livestock per day;

whereby the binding stimulates hunger in the companion animal or livestock independent of release of growth hormone throughout the period.

2. The method of claim 1, wherein the therapeutically effective amount is administered through an oral cavity of the companion animal or livestock.

3. The method of claim 2, wherein the therapeutically effective amount is administered using at least one of a spray, a pill, a tablet, and a film.

4. The method of claim 1, wherein the therapeutically effective amount is administered to the companion animal or livestock at least twice per day.

5. The method of claim 1, wherein the therapeutically effective amount is administered to the companion animal or livestock at least thrice per day.

6. The method of claim 1, wherein the capromorelin-containing composition comprises from about 1 milligram to about 4 milligrams of capromorelin per kilogram of bodyweight of the companion animal or livestock per day.

7. The method of claim 6, wherein the capromorelin-containing composition comprises from about 1.5 milligrams to about 3 milligrams of capromorelin per kilogram of bodyweight of the companion animal or livestock per day.

8. The method of claim 7, wherein the capromorelin-containing composition comprises about 2 milligrams of capromorelin per kilogram of bodyweight of the companion animal or livestock per day.

9. The method of claim 1, wherein the capromorelin-containing composition is an emulsified liquid.

10. A method of binding growth hormone secretagogue receptors (GHS-Rs) with capromorelin in the hypothalamus of a companion animal or livestock to increase lean muscle mass and to increase weight gain,
the method comprising orally administering a therapeutically effective dose of a capromorelin composition to a companion animal or livestock in need thereof at least once per day for a period of at least 30 days,
wherein the capromorelin composition comprises one or more flavoring agents or masking agents comprising at least one agent selected from the group consisting of thaumatin, sucralose, neotame, sodium saccharain, neohesperidin dihydrochalcone, rebaudioside A, steviol glycoside, licorice, glycyrrhizic acid, monoammonium glycyrrhizinate, sucrose, glucose, fructose, maltodextrin, sorbitol, maltitol, isomalt, glycerol, and a vanilla-comprising composition;
wherein the capromorelin composition comprises between about 0.5 milligrams and about 7.5 milligrams of capromorelin per kilogram of bodyweight of the companion animal or livestock per day;
wherein the therapeutically effective dose of the capromorelin composition causes the companion animal or livestock to consume a greater amount of food; and
whereby the binding stimulates hunger in the companion animal or livestock independent of growth hormone secretion sufficient to increase lean muscle mass and to increase weight gain in the companion animal or livestock throughout the period.

11. The method of claim 10, wherein the therapeutically effective dose of the capromorelin composition is administered in conjunction with a chemotherapeutic regimen.

12. The method of claim 10, wherein the capromorelin composition further comprises at least one emulsifying agent.

13. The method of claim 10, wherein the capromorelin composition is administered using one or more of a syringe, a pill, a tablet, and a film.

14. A method of binding growth hormone secretagogue receptors (GHS-Rs) with capromorelin in the hypothalamus of companion animal or livestock with chronic kidney disease (CKD) to treat weight loss,
the method comprising orally administering a therapeutically effective amount of a capromorelin-containing composition to a companion animal or livestock diagnosed chronic kidney disease and in need thereof at least once per day for a period of at least 30 days;
wherein the capromorelin-containing composition comprises from about 0.5 milligrams to about 7.5 milligrams of capromorelin per kilogram of bodyweight of the companion animal or livestock per day;
whereby the binding stimulates hunger in the companion animal or livestock independent of release of growth hormone and without the administrating increasing renal secondary hyperparathyroidism, uremic episodes, or CKD-related mortality.

15. The method of claim 14, wherein the therapeutically effective amount is administered using at least one of a spray, a pill, a tablet, and a film.

16. The method of claim 14, wherein the therapeutically effective amount is administered to the companion animal or livestock at least twice per day.

17. The method of claim 14, wherein the capromorelin-containing composition comprises from about 1 milligram to about 4 milligrams of capromorelin per kilogram of bodyweight of the companion animal or livestock per day.

18. The method of claim 14, wherein the therapeutically effective dose of the capromorelin-containing composition is administered in conjunction with a chemotherapeutic regimen.

* * * * *